US012583933B2

(12) United States Patent
Du et al.

(10) Patent No.: US 12,583,933 B2
(45) Date of Patent: Mar. 24, 2026

(54) ANTI-CD73 ANTIBODY AND USE THEREOF

(71) Applicant: BIOTHEUS INC., Guangdong (CN)

(72) Inventors: Liang Du, Shanghai (CN); Hongyan Zhang, Shanghai (CN); Lina Jin, Shanghai (CN); Yali Chen, Shanghai (CN); Jijun Yuan, Shanghai (CN); Zhenqing Zhang, Guangdong (CN); Xiaoniu Miao, Guangdong (CN); Weifeng Huang, Guangdong (CN); Yunli Jia, Guangdong (CN)

(73) Assignee: BIOTHEUS INC., Zhuhai (CN)

( * ) Notice: Subject to any disclaimer, the term of this patent is extended or adjusted under 35 U.S.C. 154(b) by 708 days.

(21) Appl. No.: 17/924,941

(22) PCT Filed: Aug. 28, 2020

(86) PCT No.: PCT/CN2020/112272
§ 371 (c)(1),
(2) Date: Nov. 11, 2022

(87) PCT Pub. No.: WO2021/227307
PCT Pub. Date: Nov. 18, 2021

(65) Prior Publication Data
US 2023/0312739 A1 Oct. 5, 2023

(30) Foreign Application Priority Data

May 12, 2020 (WO) ................ PCT/CN2020/089869

(51) Int. Cl.
*C07K 16/28* (2006.01)
*A61P 35/00* (2006.01)
(52) U.S. Cl.
CPC .......... *C07K 16/2896* (2013.01); *A61P 35/00* (2018.01); *C07K 2317/31* (2013.01); *C07K 2317/565* (2013.01); *C07K 2317/77* (2013.01)
(58) Field of Classification Search
CPC ............ C07K 16/2896; C07K 2317/31; C07K 2317/565; C07K 2317/77; C07K 2317/24; C07K 2317/33; C07K 2317/73; C07K 2317/76; C07K 2317/92; A61P 35/00; G01N 33/57492; G01N 2333/70596; G01N 33/6872; G01N 33/574; A61K 2039/505
See application file for complete search history.

(56) References Cited

U.S. PATENT DOCUMENTS 10,100,129 B2 10/2018 Lonberg et al.
2020/0148781 A1 5/2020 Zeidler et al.

FOREIGN PATENT DOCUMENTS

CN 107001474 A 8/2017
CN 110753703 A 2/2020
WO 2016/075099 A1 5/2016
WO 2016/081748 A2 5/2016
WO 2016/131950 A1 8/2016
WO 2017/064043 A1 4/2017
WO 2017/118613 A1 7/2017
WO 2018/137598 A1 8/2018

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
International Search Report and Written Opinion mailed Feb. 22, 2021, directed to International Application No. PCT/CN2020/112272; 10 pages.
Qiao et al., (Feb. 2019). "A Novel Specific Anti-CD73 Antibody Inhibits Triple-Negative Breast Cancer Cell Motility by Regulating Autophagy", International Journal of Molecular Sciences, vol. 20, No. 5.
Terp et al., (Oct. 2013). "Anti-Human CD73 Monoclonal Antibody Inhibits Metastasis Formation in Human Breast Cancer by Inducing Clustering and Internalization of CD73 Expressed on the Surface of Cancer Cells", The Journal of Immunology. vol. 191, No. 8.
European Search Report mailed May 6, 2024, directed to EP Application No. 20935744.1; 11 pages.

* cited by examiner

*Primary Examiner* — Nelson B Moseley, II
(74) *Attorney, Agent, or Firm* — Michele V. Frank; Keith G. Haddaway; Venable LLP

(57) ABSTRACT

The present invention relates to the field of disease therapy and immunology. Specifically, disclosed are an anti-CD73 antibody or an antigen-binding fragment thereof, a nucleic acid molecule encoding same, an immunoconjugate comprising same, a bispecific molecule and a pharmaceutical composition, as well as use thereof in enhancing immune response and/or treating tumors.

20 Claims, 4 Drawing Sheets

Specification includes a Sequence Listing.

Inhibition of CD73 in serum samples of
patients with melanoma by CD73 antibody

18 CD4+ T cell proliferation, the 4th day

SEQUENCE LISTING

```
<160> NUMBER OF SEQ ID NOS: 17

<210> SEQ ID NO 1
<211> LENGTH: 117
<212> TYPE: PRT
<213> ORGANISM: Artificial sequence
<220> FEATURE:
<223> OTHER INFORMATION: 13D12 VH

<400> SEQUENCE: 1

Asp Val Lys Leu Gln Glu Ser Gly Pro Ala Met Val Lys Pro Ser Gln
1               5                   10                  15

Ser Leu Ser Leu Thr Cys Thr Val Thr Gly Tyr Ser Ile Thr Ser Gly
            20                  25                  30

Tyr Asp Trp His Trp Ile Arg Leu Phe Pro Gly Asn Lys Leu Glu Trp
        35                  40                  45

Met Gly Tyr Ile Ser Tyr Ser Gly Tyr Thr Asp Tyr Ser Pro Ser Leu
    50                  55                  60

Lys Ser Arg Ile Ser Ile Thr His Asp Thr Ser Lys Asn His Phe Phe
65                  70                  75                  80

Leu Lys Leu His Ser Val Thr Thr Glu Asp Thr Ala Thr Tyr Tyr Cys
                85                  90                  95

Thr Arg Gly Asp His Ser Tyr Ala Met Asp Tyr Trp Gly Gln Gly Thr
            100                 105                 110

Ser Val Thr Val Ser
        115

<210> SEQ ID NO 2
<211> LENGTH: 107
<212> TYPE: PRT
<213> ORGANISM: Artificial sequence
<220> FEATURE:
<223> OTHER INFORMATION: 13D12 VL

<400> SEQUENCE: 2

Asp Ile Val Met Thr Gln Ser His Lys Phe Met Ser Thr Ser Val Gly
1               5                   10                  15

Asp Arg Val Ser Ile Thr Cys Lys Ala Ser Gln Ala Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Ser Arg His Thr Gly Val Pro Asp Arg Phe Thr Gly
    50                  55                  60

Ser Arg Ser Gly Thr Asp Phe Thr Leu Thr Ile Ser Ser Val Gln Ser
65                  70                  75                  80

Glu Asp Leu Ala Asp Tyr Phe Cys Gln Gln Tyr Ser Ser Tyr Pro Leu
                85                  90                  95
```

```
Thr Phe Gly Gly Gly Thr Asn Leu Glu Ile Lys
          100                 105

<210> SEQ ID NO 3
<211> LENGTH: 8
<212> TYPE: PRT
<213> ORGANISM: Artificial sequence
<220> FEATURE:
<223> OTHER INFORMATION: 13D12 HCDR1

<400> SEQUENCE: 3

Gly Tyr Ser Ile Thr Ser Gly Tyr
1               5

<210> SEQ ID NO 4
<211> LENGTH: 5
<212> TYPE: PRT
<213> ORGANISM: Artificial sequence
<220> FEATURE:
<223> OTHER INFORMATION: 13D12 HCDR2

<400> SEQUENCE: 4

Ser Tyr Ser Gly Tyr
1               5

<210> SEQ ID NO 5
<211> LENGTH: 9
<212> TYPE: PRT
<213> ORGANISM: Artificial sequence
<220> FEATURE:
<223> OTHER INFORMATION: 13D12 HCDR3

<400> SEQUENCE: 5

Gly Asp His Ser Tyr Ala Met Asp Tyr
1               5

<210> SEQ ID NO 6
<211> LENGTH: 11
<212> TYPE: PRT
<213> ORGANISM: Artificial sequence
<220> FEATURE:
<223> OTHER INFORMATION: 13D12 LCDR1

<400> SEQUENCE: 6

Lys Ala Ser Gln Ala Val Gly Thr Ala Val Ala
1               5                 10

<210> SEQ ID NO 7
<211> LENGTH: 7
<212> TYPE: PRT
<213> ORGANISM: Artificial sequence
<220> FEATURE:
<223> OTHER INFORMATION: 13D12 LCDR2

<400> SEQUENCE: 7

Trp Ala Ser Ser Arg His Thr
1               5

<210> SEQ ID NO 8
<211> LENGTH: 9
<212> TYPE: PRT
<213> ORGANISM: Artificial sequence
<220> FEATURE:
<223> OTHER INFORMATION: 13D12 LCDR3

<400> SEQUENCE: 8
```

```
Gln Gln Tyr Ser Ser Tyr Pro Leu Thr
1               5

<210> SEQ ID NO 9
<211> LENGTH: 118
<212> TYPE: PRT
<213> ORGANISM: Artificial sequence
<220> FEATURE:
<223> OTHER INFORMATION: 7002-01 VH

<400> SEQUENCE: 9

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Asp Trp His Trp Ile Arg Gln His Pro Gly Lys Gly Leu Glu Trp
        35                  40                  45

Met Gly Tyr Ile Ser Tyr Ser Gly Tyr Thr Asp Tyr Asn Pro Ser Leu
    50                  55                  60

Lys Ser Arg Ile Thr Ile Ser His Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Thr Arg Gly Asp His Ser Tyr Ala Met Asp Tyr Trp Gly Gln Gly Thr
            100                 105                 110

Leu Val Thr Val Ser Ser
        115

<210> SEQ ID NO 10
<211> LENGTH: 107
<212> TYPE: PRT
<213> ORGANISM: Artificial sequence
<220> FEATURE:
<223> OTHER INFORMATION: 7002-01 VL

<400> SEQUENCE: 10

Ala Ile Gln Met Thr Gln Ser His Ser Ser Leu Ser Ala Ser Val Gly
1               5                   10                  15

Asp Arg Val Thr Ile Thr Cys Lys Ala Ser Gln Ala Val Gly Thr Ala
            20                  25                  30

Val Ala Trp Tyr Gln Gln Lys Pro Gly Lys Ser Pro Lys Leu Leu Ile
        35                  40                  45

Tyr Trp Ala Ser Ser Arg His Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Leu
                85                  90                  95

Thr Phe Gly Gly Gly Thr Lys Val Glu Ile Lys
            100                 105

<210> SEQ ID NO 11
<211> LENGTH: 351
<212> TYPE: DNA
<213> ORGANISM: Artificial sequence
<220> FEATURE:
<223> OTHER INFORMATION: 13D12 VH nucleic acid sequence

<400> SEQUENCE: 11
gatgtgaagc tgcaggagag cggaccagct atggtgaagc ctagccagag cctgagcctg     60
```

-continued

```
acttgcaccg tgaccggcta cagcatcacc agcggctacg attggcattg gatcagactg      120
ttcccaggca acaagctcga gtggatgggc tacatcagct acagcggcta caccgactac      180
agccctagcc tgaagagccg gatcagcatc acccacgaca ccagcaagaa ccacttcttc      240
ctgaagctgc acagcgtgac aaccgaggac accgccacct actattgcac cagaggcgac      300
cacagctacg ccatggacta ttggggccag ggaacaagcg tgacagtgtc t              351
```

```
<210> SEQ ID NO 12
<211> LENGTH: 321
<212> TYPE: DNA
<213> ORGANISM: Artificial sequence
<220> FEATURE:
<223> OTHER INFORMATION: 13D12 VL nucleic acid sequence

<400> SEQUENCE: 12
gacatcgtga tgacccagag ccacaagttc atgagcacca gcgtgggaga cagagtgtcc       60
atcacttgca aggcctctca ggccgtggga acagccgttg cttggtacca gcagaagccc      120
ggacagagcc ccaagctgct gatctattgg gccagctcta gacacacagg agtgccagac      180
agattcaccg gcagcagaag cggaaccgac ttcaccctga ccatcagcag cgtgcagagc      240
gaagacctgg ccgactactt ctgccagcag tacagcagct accccctgac atttggcggc      300
ggcaccaacc tggagatcaa g                                               321
```

```
<210> SEQ ID NO 13
<211> LENGTH: 354
<212> TYPE: DNA
<213> ORGANISM: Artificial sequence
<220> FEATURE:
<223> OTHER INFORMATION: 7002-01 VH nucleic acid sequence

<400> SEQUENCE: 13
caggtccaac tccaagagag cggccccggc ctcgtcaaac ccagccaaac actctccctc       60
acctgcacag tcagcggcta cagcatcaca agcggatacg actggcactg gatcagacaa      120
caccccggca aaggcctgga gtggatgggc tatatcagct acagcggcta caccgactac      180
aacccaagcc tgaaaagcag aatcacaatc agccacgaca ccagcaagaa ccagttcagc      240
ctcaagctga gcagcgtgac cgccgcagac accgccgtct actattgcac cagaggcgac      300
cactcctacg ccatggacta ctggggccag ggcaccctcg tgaccgtgtc cagc           354
```

```
<210> SEQ ID NO 14
<211> LENGTH: 321
<212> TYPE: DNA
<213> ORGANISM: Artificial sequence
<220> FEATURE:
<223> OTHER INFORMATION: 7002-01 VL nucleic acid sequence

<400> SEQUENCE: 14
gctattcaaa tgacccagtc ccattcctcc ctgtccgcct ccgtgggcga ccgagtgacc       60
attacctgta aagccagcca agccgtcgga accgccgtcg catggtacca acaaaaaccc      120
ggcaaaagcc ccaaactcct catctactgg gccagtagca gacacaccgg cgtgcccagc      180
agattcagcg gaagcagatc cggcaccgac ttcaccctga ccatcagcag cctgcaaccc      240
gaggacttcg ccacctactt ctgtcagcag tacagcagct accccctcac cttcggaggc      300
ggcaccaagg tggagatcaa a                                               321
```

```
<210> SEQ ID NO 15
```

<211> LENGTH: 330
<212> TYPE: PRT
<213> ORGANISM: Artificial sequence
<220> FEATURE:
<223> OTHER INFORMATION: Human IgG1-TM heavy chain constant region

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Ser Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 107
<212> TYPE: PRT
<213> ORGANISM: Artificial sequence
<220> FEATURE:
<223> OTHER INFORMATION: Human kappa light chain constant region -continued

<400> SEQUENCE: 16

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 17
<211> LENGTH: 574
<212> TYPE: PRT
<213> ORGANISM: Artificial sequence
<220> FEATURE:
<223> OTHER INFORMATION: Human CD73

<400> SEQUENCE: 17

```
Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
```

-continued

```
              245              250              255

Glu Val Pro Ala Gly Lys Tyr Pro Phe Ile Val Thr Ser Asp Asp Gly
            260              265              270

Arg Lys Val Pro Val Val Gln Ala Tyr Ala Phe Gly Lys Tyr Leu Gly
            275              280              285

Tyr Leu Lys Ile Glu Phe Asp Glu Arg Gly Asn Val Ile Ser Ser His
        290              295              300

Gly Asn Pro Ile Leu Leu Asn Ser Ser Ile Pro Glu Asp Pro Ser Ile
305              310              315              320

Lys Ala Asp Ile Asn Lys Trp Arg Ile Lys Leu Asp Asn Tyr Ser Thr
            325              330              335

Gln Glu Leu Gly Lys Thr Ile Val Tyr Leu Asp Gly Ser Ser Gln Ser
            340              345              350

Cys Arg Phe Arg Glu Cys Asn Met Gly Asn Leu Ile Cys Asp Ala Met
            355              360              365

Ile Asn Asn Asn Leu Arg His Thr Asp Glu Met Phe Trp Asn His Val
        370              375              380

Ser Met Cys Ile Leu Asn Gly Gly Gly Ile Arg Ser Pro Ile Asp Glu
385              390              395              400

Arg Asn Asn Gly Thr Ile Thr Trp Glu Asn Leu Ala Ala Val Leu Pro
            405              410              415

Phe Gly Gly Thr Phe Asp Leu Val Gln Leu Lys Gly Ser Thr Leu Lys
            420              425              430

Lys Ala Phe Glu His Ser Val His Arg Tyr Gly Gln Ser Thr Gly Glu
            435              440              445

Phe Leu Gln Val Gly Gly Ile His Val Val Tyr Asp Leu Ser Arg Lys
        450              455              460

Pro Gly Asp Arg Val Val Lys Leu Asp Val Leu Cys Thr Lys Cys Arg
465              470              475              480

Val Pro Ser Tyr Asp Pro Leu Lys Met Asp Glu Val Tyr Lys Val Ile
            485              490              495

Leu Pro Asn Phe Leu Ala Asn Gly Gly Asp Gly Phe Gln Met Ile Lys
            500              505              510

Asp Glu Leu Leu Arg His Asp Ser Gly Asp Gln Asp Ile Asn Val Val
            515              520              525

Ser Thr Tyr Ile Ser Lys Met Lys Val Ile Tyr Pro Ala Val Glu Gly
        530              535              540

Arg Ile Lys Phe Ser Thr Gly Ser His Cys His Gly Ser Phe Ser Leu
545              550              555              560

Ile Phe Leu Ser Leu Trp Ala Val Ile Phe Val Leu Tyr Gln
            565              570
```

1

ANTI-CD73 ANTIBODY AND USE THEREOF

CROSS-REFERENCE TO RELATED APPLICATIONS

This application is a National Phase of International Application No. PCT/CN2020/112272, filed Aug. 28, 2020, which claims priority to PCT/CN2020/089869, filed May 12, 2020, the entire contents of which are hereby incorporated by reference in its entirety.

The instant application contains a Sequence Listing which has been submitted electronically in ASCII format and is hereby incorporated by reference in its entirety. Said ASCII copy, created on May 12, 2023, is named SequenceListing141279-570345.txt and is 16,941 bytes in size.

TECHNICAL FIELD

The present invention relates to the field of disease treatment and immunology, in particular, the present invention relates to an anti-CD73 antibody or antigen-binding fragment thereof, a nucleic acid molecule encoding the same, an immunoconjugate, bispecific molecule and pharmaceutical composition comprising the same, and a use thereof for enhancing an immune response and/or treating a tumor.

BACKGROUND ART

In recent years, the rapid development of cancer immunotherapy has given the scientific community a better understanding of tumor biology and immunology. The tumor microenvironment is a dynamic microenvironment that includes cancer cells, immune cells, fibroblasts, myofibroblasts, cytokines, blood vessels, and extracellular matrix. Tumors are often under hypoxic conditions, and the environment is also deficient in glucose and other nutrients. In order to survive, cancer cells reorganize their metabolic mechanism in such an environment. Among them, regulating purine metabolism is a very critical step, especially increasing the expression of cluster of differentiation 73 (CD73, also known as extracellular-5'-nucleotidase). CD73 is a glycosylphosphatidylinositol-anchored cell surface protein commonly expressed on subsets of endothelial and hematopoietic cells (Misumi Y et al., European Journal of Biochemistry 1990; 191(3): 563-9). Extracellularly, CD73, together with CD39, regulates the conversion of adenosine triphosphate to adenosine, and this step of CD73-catalyzed dephosphorylation of adenosine monophosphate to adenosine is the rate-determining step on the aforementioned conversion axis (Resta R et al., Immunological Reviews 1998; 161: 95-109).

In response to cell death and cellular stress, cells release ATP to activate immune responses. In contrast, the hydrolysis of ATP to adenosine acts as an inverse feedback mechanism and leads to suppression of the immune response. Adenosine is a widely studied signaling molecule that mediates its biological effects via several receptors, including A1, A2A, A2B and A3. Adenosine is known to regulate the proliferation and migration of many cancers, and extracellular adenosine accumulates in cancerous tissues and constitutes an important mechanism of tumor immune escape (Bin Z. Cancer Research 2010; 70: 6407-6411). Among other effects, tumor-derived adenosine profoundly inhibits infiltrating effector T cells through adenylate cyclase-activated A2A receptors.

CD73 has been reported to be expressed on many different tumors, including melanoma, colon cancer, lung cancer, ovarian cancer, bladder cancer, glioma, glioblastoma, thyroid cancer, esophageal cancer, prostate cancer, and breast cancer. CD73 is a potent prognostic biomarker in solid tumors, and CD73 overexpression is associated with shorter overall survival or shorter progression-free survival (Rong W et al., Oncotarget 2017; 8(34): 57327-57336). CD73 expression in cancer is associated with increased tumor cell proliferation, migration, neovascularization, invasiveness, metastasis, and it has been shown that knockdown using siRNA or overexpression of CD73 on tumor cells can modulate tumor growth and metastasis (Paul B et al., PNAS 2013; 110(36): 14711-14716); CD73-/- mice are protected from transplanted and spontaneous tumors (John S et al., Cancer Research 2010; 71: 2892-2900). In addition to the reported regulation of cell-cell and cell-matrix interactions on tumor cells by CD73, CD73 expression and activity have also been associated with attenuated T cell responses (Dachuan J et al., Cancer Res 2010; 70: 2245-55). CD73 has also been regulated in resistance to chemotherapeutic drugs, such as anthracyclines (Loi, S et al., PNAS 2013; 110: 11091-11096), as well as resistance to induction of apoptosis by tumor necrosis factor-related apoptosis-inducing ligand (TRAIL). Thus, CD73 can regulate cancer progression in both direct and indirect ways, highlighting its potential as a novel therapeutic target.

In addition, cancer immune checkpoint inhibitor drugs have shown promising efficacy in a variety of cancer patients in recent years, however, a substantial proportion of patients remain unresponsive to these treatments, and one-third of patients relapse after initial response (adaptive drug resistance), which indicates that multiple immunosuppressive mechanisms coexist in the tumor microenvironment, and drug targets those can be used synergistically or in combination, which are the current research hotspots in cancer immunology.

Therefore, CD73 has shown its potential as an anti-tumor therapeutic target, either as a single agent or as a combination therapy.

CONTENTS OF THE PRESENT INVENTION

The antibody of the present invention can specifically bind to membrane-bound CD73 on the surface of tumor cells and CD73 in non-membrane-bound form, inhibit the enzymatic activity of CD73, enhance immune response, and has good anti-tumor activity and better functional characteristics as compared to known anti-CD73 antibodies. Therefore, the antibody of the present invention has the potential for preventing and/or treating a tumor, and is a choice for clinical tumor immunotherapy drug.

sAntibody of the Present Invention

Accordingly, in one aspect, the present invention provides an antibody or antigen-binding fragment thereof capable of specifically binding to CD73, the antibody or antigen-binding fragment thereof comprising:

the following three heavy chain variable region CDRs:

(i) VHCDR1, which consists of the following sequence: SEQ ID NO: 3, or a sequence having a substitution, deletion or addition of one or more amino acids (e.g., a substitution, deletion or addition of 1, 2 or 3 amino acids) as compared thereto, (ii) VHCDR2, which consists of the following sequence: SEQ ID NO: 4, or a sequence having a substitution, deletion or addition of one or more amino acids (e.g., a substitution, deletion or addition of 1, 2 or 3 amino acids) as compared thereto, and (iii) VHCDR3, which consists of the following sequence: SEQ ID NO: 5, or a sequence having a substitution, deletion or addition of one or more amino acids (e.g., a substitution, deletion or addition of 1, 2 or 3 amino acids) as compared thereto;

and, the following three light chain variable region CDRs:

(iv) VLCDR1, which consists of the following sequence: SEQ ID NO: 6, or a sequence having a substitution, deletion or addition of one or more amino acids (e.g., a substitution, deletion or addition of 1, 2 or 3 amino acids) as compared thereto, (v) VLCDR2, which consists of the following sequence: SEQ ID NO: 7, or a sequence having a substitution, deletion or addition of one or more amino acids (e.g., a substitution, deletion or addition of 1, 2 or 3 amino acids) as compared thereto, and (vi) VLCDR3, which consists of the following sequence: SEQ ID NO: 8, or a sequence having a substitution, deletion or addition of one or more amino acids (e.g., a substitution, deletion or addition of 1, 2 or 3 amino acids) as compared thereto.

In certain embodiments, the substitution described in any of (i) to (vi) is a conservative substitution.

In certain embodiments, the antibody or antigen-binding fragment thereof of the present invention is capable of binding to human CD73, for example, membrane-bound human CD73 and/or soluble human CD73.

In another aspect, the present invention provides an antibody or antigen-binding fragment thereof capable of specifically binding to CD73, the antibody or antigen-binding fragment thereof comprising:

The following three heavy chain variable region CDRs: VHCDR1, VHCDR2 and VHCDR3 contained in the heavy chain variable region set forth in SEQ ID NO: 1, and the following three light chain variable region CDRs: VLCDR1, VLCDR2 and VLCDR3 contained in the light chain variable region set forth in SEQ ID NO:2.

In certain embodiments, the three CDRs contained in the heavy chain variable region and the three CDRs contained in the light chain variable region are defined by the Kabat, Chothia, or IMGT numbering system.

In certain embodiments, the antibody or antigen-binding fragment thereof of the present invention is capable of binding to human CD73, for example, membrane-bound human CD73 and/or soluble human CD73.

In certain embodiments, the antibody or antigen-binding fragment thereof of the present invention comprises a heavy chain variable region and a light chain variable region, in which the heavy chain variable region comprises an amino acid sequence set forth in SEQ ID NO: 1 or a sequence having a sequence identity of at least about 85%, 90%, 95% or 99% as compared thereto, and the light chain variable region comprises an amino acid sequence set forth in SEQ ID NO: 2 or a sequence having a sequence identity of at least about 85%, 90%, 95% or 99% as compared thereto.

In certain embodiments, the antibody or antigen-binding fragment thereof of the present invention comprises a framework region sequence derived from a human immunoglobulin, the framework region optionally comprising one or more (e.g., 1, 2, 3, 4, 5, 6, 7, 8, 9, or 10) back mutations from human residues to the corresponding murine residues. In certain embodiments, the antibody or antigen-binding fragment thereof comprises: a heavy chain framework region sequence derived from a human heavy chain germline sequence (i.e., an amino acid sequence encoded by a human heavy chain germline gene), and a light chain framework region sequence derived from a human light chain germline sequence (i.e., an amino acid sequence encoded by a human light chain germline gene), the heavy chain framework region and/or the light chain framework region optionally comprising one or more (e.g., 1, 2, 3, 4, 5, 6, 7, 8, 9, or 10) back mutations from human residues to the corresponding murine residues.

In certain embodiments, the antibody or antigen-binding fragment thereof of the present invention comprises: a heavy chain framework region sequence derived from a heavy chain germline sequence, and a light chain framework region sequence derived from a light chain germline sequence, the heavy chain framework region and/or the light chain framework region optionally comprise one or more (e.g., 1, 2, 3, 4, 5, 6, 7, 8, 9, or 10) back mutations from human residues to the corresponding murine residues.

In certain embodiments, the antibody or antigen-binding fragment thereof of the present invention comprises a heavy chain variable region and a light chain variable region, the heavy chain variable region comprising an amino acid sequence set forth in SEQ ID NO: 9 or a sequence having a sequence identity of at least about 85%, 90%, 95% or 99% as compared thereto, and the light chain variable region comprising an amino acid sequence set forth in SEQ ID NO: 10 or a sequence having a sequence identity of at least about 85%, 90%, 95% or 99% as compared thereto.

In certain embodiments, the antibody or antigen-binding fragment thereof of the present invention may further comprise a constant region derived from a mammalian (e.g., murine or human) immunoglobulin. In certain embodiments, the heavy chain of the antibody or antigen-binding fragment thereof comprises a heavy chain constant region derived from a mammalian (e.g., murine or human) immunoglobulin (e.g., IgG1, IgG2, IgG3, or IgG4), and the light chain of the antibody or antigen-binding fragment thereof comprises a light chain constant region derived from a mammalian (e.g., murine or human) immunoglobulin (e.g., κ or λ).

In certain embodiments, the heavy chain of the antibody or antigen-binding fragment thereof of the present invention comprises a heavy chain constant region (CH) of a human immunoglobulin, or a variant thereof, which, compared to the sequence from which it is derived, has a substitution, deletion or addition of one or more amino acids (e.g., a substitution, deletion or addition of up to 20, up to 15, up to 10, or up to 5 amino acids; e.g., a substitution, deletion or addition of 1, 2, 3, 4 or 5 amino acids); and/or, the light chain of the antibody or antigen-binding fragment thereof of the present invention comprises a light chain constant region (CL) of a human immunoglobulin, or a variant thereof, which, compared to the sequence from which it is derived, has a conservative substitution of up to 20 amino acids (e.g., a conservative substitution of up to 15, up to 10, or up to 5 amino acids; e.g., a conservative substitution of 1, 2, 3, 4 or 5 amino acids).

In certain embodiments, the constant region may comprise an amino acid mutation to alter one or more of the following properties of the antibody of the present invention: Fc receptor binding, antibody glycosylation, number of cysteine residues, effector cell function or complement function, etc. Change in function can be produced by substituting at least one amino acid residue in the antibody constant region with a different residue, for example, change (e.g., decrease) in effector function can be produced by changing the affinity of the antibody to effector ligand (e.g., FcR or complement C1q).

Methods for substituting amino acid residues in the Fc region of an antibody to alter its effector function are known in the art. The Fc region of antibody mediates several important effector functions such as ADCC, phagocytosis, CDC, etc. In some cases, these effector functions are required for therapeutic antibodies; but in other cases, these effector functions may be unnecessary or even detrimental, depending on the intended purpose.

Thus, in certain embodiments, the antibody or antigen-binding fragment thereof of the present invention has a decreased or even eliminated effector function (e.g., ADCC and/or CDC activity). In such embodiments, the antibody or antigen-binding fragment thereof of the present invention may comprise a variant of a human IgG heavy chain constant region, in which, compared to the wild-type sequence from which it is derived, the variant has at least one, at least two or all three of the following substitutions: L234F, L235E, P331S (the amino acid positions mentioned above are positions according to the EU numbering system), see, for example, Acta Cryst. (2008). D64, 700-704.

In certain exemplary embodiments, the antibody or antigen-binding fragment thereof of the present invention comprises a human wild-type IgG1 heavy chain constant region. In such embodiments, the antibody or antigen-binding fragment thereof of the present invention has ADCC and CDC activities.

In certain exemplary embodiments, the antibody or antigen-binding fragment thereof of the present invention comprises a variant of a human IgG1 heavy chain constant region, in which, compared to the wild-type sequence from which it is derived, the variant has the following substitutions: L234F, L235E, P331S (position according to the EU numbering system), such as the heavy chain constant region set forth in SEQ ID NO: 15. In such embodiments, the antibody or antigen-binding fragment thereof of the present invention has an eliminated or decreased ADCC and/or CDC activity.

In certain preferred embodiments, the heavy chain of the antibody or antigen-binding fragment thereof of the present invention comprises a variant of a human immunoglobulin heavy chain constant region (CH), in which, compared to the wild-type sequence from which it is derived, the variant has an essentially unchanged effector function. In such embodiments, the variant may have a conservative substitution of up to 20 amino acids (e.g., a conservative substitution of up to 15, up to 10, or up to 5 amino acids; e.g., a conservative substitution of 1, 2, 3, 4 or 5 amino acids).

In certain exemplary embodiments, the antibody or antigen-binding fragment thereof of the present invention comprises a human κ light chain constant region, for example, a light chain constant region set forth in SEQ ID NO:16.

In certain exemplary embodiments, the antibody or antigen-binding fragment thereof of the present invention comprises a heavy chain constant region (CH) set forth in SEQ ID NO: 15; and/or a light chain constant region (CL) set forth in SEQ ID NO: 16.

In certain embodiments, the antibody of the present invention is a murine antibody, chimeric antibody, humanized antibody, bispecific antibody or multispecific antibody. In certain embodiments, the antigen-binding fragment of the present invention is selected from the group consisting of Fab, Fab', (Fab')₂, Fv, disulfide-linked Fv, scFv, diabody, and single domain antibody (sdAb).

In certain embodiments, the antibody or antigen-binding fragment thereof of the present invention possesses one or more of the following characteristics:

(a) binding to membrane-bound human CD73 or soluble human CD73, or both; for example, the membrane-bound human CD73 is expressed on the surface of a tumor cell;

(b) inhibiting or reducing an enzymatic activity of CD73 (e.g., membrane-bound human CD73 or soluble human CD73); for example, inhibiting or reducing human CD73-mediated conversion of adenosine monophosphate (AMP) to adenosine, for example, as determined by CellTiter Glo (CTG) assay (e.g., the method described in Example 6);

(c) increasing proliferation of an anti-CD3/anti-CD28 stimulated T cell (e.g., CD4+ T cell) in the presence of adenosine monophosphate (AMP); for example, as determined by the method described in Example 8;

(d) inducing internalization of CD73 into a cell (e.g., tumor cell) that expresses CD73 on its surface by antibody-mediated receptor internalization; for example, with an internalization level of at least 10% (e.g., at least 15%, at least 20% or more) as measured by FACS or flow cytometry (e.g., the method of Example 7);

(e) binding to soluble human CD73 with an EC50 of less than about 0.01 μg/ml or less; the EC50 being determined by ELISA technique;

(f) binding to soluble human CD73 with a KD of less than about 0.5 nM or less; the KD being measured by Biacore;

(g) reducing an adenosine level in a CD73-expressing tumor cell;

(h) stimulating an immune response; for example, stimulating an immune response against a tumor (e.g., a tumor expressing CD73);

(i) preventing and/or treating a tumor (e.g., a CD73-expressing tumor).

In certain embodiments, the antibody or antigen-binding fragment thereof is 13D12 or antigen-binding fragment thereof, a chimeric antibody thereof, or a humanized antibody thereof, or a functional variant thereof, in which the variant substantially retains a biological function of the antibody or antigen-binding fragment thereof from which it is derived.

In the present invention, the antibody or antigen-binding fragment thereof of the present invention may comprise a variant, in which, compared to the antibody or antigen-binding fragment thereof from which it is derived, the variant has a difference in only a conservative substitution of one or more amino acid residues (e.g., a conservative substitution of up to 20, up to 15, up to 10, or up to 5 amino acids), or has a sequence identity of at least 85%, at least 90%, at least 95%, at least 96%, at least 97%, at least 98%, at least 99%, or 100% as compared to the antibody or antigen-binding fragment thereof from which it is derived, and substantially retains the above-mentioned biological function of the antibody or antigen-binding fragment thereof from which it is derived.

Preparation of Antibody

The antibody of the present invention can be prepared by various methods known in the art, such as by genetic engineering recombinant techniques. For example, DNA molecules encoding the heavy and light chain genes of the antibody of the present invention are obtained by chemical synthesis or PCR amplification. The resulting DNA molecule is inserted into an expression vector and then transfected into a host cell. Then, the transfected host cell is cultured under specific conditions and expresses the antibody of the present invention.

The antigen-binding fragments of the present invention can be obtained by hydrolysis of intact antibody molecules (see, Morimoto et al., J. Biochem. Biophys. Methods 24:107-117 (1992) and Brennan et al., Science 229:81 (1985)). Alternatively, these antigen-binding fragments can also be produced directly by recombinant host cells (reviewed in Hudson, Curr. Opin. Immunol. 11:548-557 (1999); Little et al., Immunol. Today, 21:364-370 (2000)). For example, Fab' fragments can be obtained directly from host cells; Fab' fragments can be chemically coupled to form F(ab')2 fragments (Carter et al., Bio/Technology, 10: 163-167 (1992)). In addition, Fv, Fab or F(ab')2 fragments can also be directly isolated from the culture medium of recombinant host cells. Other techniques for preparing these antigen-binding fragments are well known to those of ordinary skill in the art.

Accordingly, in another aspect, the present invention provides an isolated nucleic acid molecule, which comprises a nucleotide sequence encoding the antibody or antigen-binding fragment thereof of the present invention, or a heavy chain variable region and/or light chain variable region thereof. In certain embodiments, the isolated nucleic acid molecule encodes the antibody or antigen-binding fragment thereof of the present invention, or the heavy chain variable region and/or light chain variable region thereof.

In certain embodiments, the isolated nucleic acid molecule comprises a first nucleotide sequence encoding the heavy chain variable region of the antibody or antigen-binding fragment thereof of the present invention, and/or a second nucleotide sequence encoding the light chain variable region of the antibody or antigen-binding fragment thereof of the present invention.

In certain embodiments, the first nucleotide sequence comprises a sequence selected from the group consisting of: (a) a nucleotide sequence set forth in SEQ ID NO: 11, or (b) a sequence substantially identical to the nucleotide sequence set forth in (a) (e.g., a sequence having a sequence identity of at least about 85%, 90%, 95%, 99% or more as compared to the nucleotide sequence set forth in (a), or a sequence having a substitution of one or more nucleotides as compared to the nucleotide sequence set forth in (a)), or (c) a sequence that differs from the nucleotide sequence set forth in (a) by no more than 3, 6, 15, 30 or 45 nucleotides; and the second nucleotide sequence comprises a sequence selected from the group consisting of: (d) a nucleotide sequence set forth in SEQ ID NO: 12, or (e) a sequence substantially identical to the nucleotide sequence set forth in (d) (e.g., a sequence having a sequence identity of at least about 85%, 90%, 95%, 99% or more as compared to the nucleotide sequence set forth in (d), or a sequence having a substitution of one or more nucleotides as compared to the nucleotide sequence set forth in (d)), or (f) a sequence that differs from the nucleotide sequence set forth in (d) by no more than 3, 6, 15, 30 or 45 nucleotides.

In certain embodiments, the first nucleotide sequence comprises a sequence selected from the group consisting of: (a) a nucleotide sequence set forth in SEQ ID NO: 13, or (b) a sequence substantially identical to the nucleotide sequence set forth in (a) (e.g., a sequence having a sequence identity of at least about 85%, 90%, 95%, 99% or more as compared to the nucleotide sequence set forth in (a), or a sequence having a substitution of one or more nucleotides as compared to the nucleotide sequence set forth in (a)), or (c) a sequence that differs from the nucleotide sequence set forth in (a) by no more than 3, 6, 15, 30 or 45 nucleotides; and the second nucleotide sequence comprises a sequence selected from the group consisting of: (d) a nucleotide sequence set forth in SEQ ID NO: 14, or (e) a sequence substantially identical to the nucleotide sequence set forth in (d) (e.g., a sequence having a sequence identity of at least about 85%, 90%, 95%, 99% or more as compared to the nucleotide sequence set forth in (d), or a sequence having a substitution of one or more nucleotides as compared to the nucleotide sequence set forth in (d)), or (f) a sequence that differs from the nucleotide sequence set forth in (d) by no more than 3, 6, 15, 30 or 45 nucleotides.

In certain embodiments, the isolated nucleic acid molecule comprises a first nucleotide sequence encoding the heavy chain of the antibody or antigen-binding fragment thereof of the present invention, and/or a second nucleotide sequence encoding the light chain of the antibody or antigen-binding fragment thereof of the present invention.

In another aspect, the present invention provides a vector (e.g., a cloning vector or an expression vector), which comprises the isolated nucleic acid molecule of the present invention. In certain embodiments, the vector of the present invention is, for example, plasmid, cosmid, phage, and the like. In certain embodiments, the vector is capable of expressing the antibody or antigen-binding fragment thereof of the present invention in a subject (e.g., a human).

In another aspect, the present invention provides a host cell, which comprises the isolated nucleic acid molecule of the present invention or the vector of the present invention. Such host cell includes, but is not limited to, prokaryotic cell such as *E. coli* cell, and eukaryotic cell such as yeast cell, insect cell, plant cell, and animal cell (e.g., mammalian cell, such as mouse cell, human cell, etc.). In certain embodiments, the host cell of the present invention is a mammalian cell, for example, CHO (e.g., CHO-K1, CHO-S, CHO DG44).

In another aspect, there is provided a method for preparing the antibody or antigen-binding fragment thereof of the present invention, which comprises, culturing the host cell of the present invention under conditions that permit the expression of the antibody or antigen-binding fragment thereof, and recovering the antibody or antigen-binding fragment thereof from a cell culture of the cultured host.

Derivatized Antibody

The antibody or antigen-binding fragment thereof of the present invention can be derivatized, for example, linked to another molecule (e.g., another polypeptide or protein). Generally, the derivatization (e.g., labeling) of the antibody or antigen-binding fragment thereof does not adversely affect its binding to CD73. Accordingly, the antibody or antigen-binding fragment thereof of the present invention is also intended to include such derivatization forms. For example, the antibody or antigen-binding fragment thereof of the present invention can be functionally linked (by chemical coupling, genetic fusion, non-covalent attachment, or otherwise) to one or more other molecular moieties, such as another antibody (e.g., to form a bispecific antibody), detection reagent, pharmaceutical reagent, and/or protein or polypeptide (e.g., avidin or polyhistidine tag) capable of mediating the binding of the antibody or antigen-binding fragment to another molecule. In addition, the antibody or antigen-binding fragment thereof of the present invention can also be derivatized with a chemical group such as polyethylene glycol (PEG), methyl or ethyl, or glycosyl. These groups can be used to improve the biological properties of the antibody, such as increasing serum half-life.

Thus, in certain embodiments, the antibody or antigen-binding fragment thereof of the present invention bears a detectable label, such as an enzyme, radionuclide, fluorescent dye, luminescent substance (e.g., chemiluminescent substance), or biotin. The detectable label of the present invention can be any substance detectable by fluorescent, spectroscopic, photochemical, biochemical, immunological, electrical, optical or chemical means. Such labels are well known in the art, examples of which include, but are not limited to, enzyme (e.g., horseradish peroxidase, alkaline phosphatase, β-galactosidase, urease, glucose oxidase, etc.), radionuclides (e.g., $^3H$, $^{125}I$, $^{35}S$, $^{14}C$, or $^{32}P$), fluorescent dye (e.g., fluorescein isothiocyanate (FITC), fluorescein, tetramethylrhodamine isothiocyanate (TRITC), phycoerythrin (PE), Texas red, rhodamine, quantum dot or cyanine derivative (e.g., Cy7, Alexa 750)), luminescent substance (e.g., chemiluminescent substance such as acridine ester), magnetic bead (e.g., Dynabeads®), calorimetric label such as colloidal gold or colored glass or plastic (e.g., polystyrene, polypropylene, latex, etc.) bead, and biotin for binding to the aforementioned detectable label-modified avidin (e.g., streptavidin, etc.). The detectable label as described above can be detected by methods known in the art. For example, radiolabels can be detected using photographic film or a scintillation calculator, and fluorescent labels can be detected using a light detector to detect the emitted light. Enzyme labels are generally detected by providing a substrate to the enzyme and detecting the reaction product produced by the action of the enzyme on the substrate, and calorimetric labels are detected by simply visualizing the colored labels. In certain embodiments, such labels can be suitable for use in immunological detection (e.g., enzyme-linked immunosorbent assay, radioimmunoassay, fluorescent immunoassay, chemiluminescence immunoassay, etc.). In certain embodiments, a detectable label as described above can be attached to the antibody or antigen-binding fragment thereof of the present invention via a linker of various lengths to reduce potential steric hindrance.

Bispecific or Multispecific Molecule

The antibody or antigen-binding fragment thereof of the present invention can be used to form a bispecific or multispecific molecule. The antibody or antigen-binding fragment thereof of the present invention may be part of a bispecific or multispecific molecule, the bispecific or multispecific molecule comprising a second functional module (e.g., a second antibody) having a different binding specificity as compared to the antibody or antigen-binding fragment thereof of the present invention, thereby capable of binding to at least two different binding sites and/or target molecules. For example, the antibody or antigen-binding fragment thereof of the present invention can be linked to a second antibody or antigen-binding fragment thereof capable of specifically binding to any protein that can be used as a potential target for combination therapy. To generate such bispecific or multispecific molecule, the antibody or antigen-binding fragment thereof of the present invention can be linked (e.g., by chemical conjugation, genetic fusion, non-covalent association, or otherwise) to one or more additional binding molecules (e.g., additional antibody, antibody fragment, peptide, or binding mimetic).

Accordingly, in another aspect, the present invention provides a bispecific or multispecific molecule, which comprises the antibody or antigen-binding fragment thereof of the present invention.

In certain embodiments, the bispecific or multispecific molecule specifically binds to CD73 (e.g., membrane-bound human CD73 and/or soluble human CD73), and additionally specifically binds to one or more additional targets.

In certain embodiments, the bispecific or multispecific molecule further comprises at least one kind of molecule (e.g., a second antibody) having a second binding specificity for a second target.

Immunoconjugate

The antibody or antigen-binding fragment thereof of the present invention can be linked to a therapeutic agent to form an immunoconjugate. Because the immunoconjugate has an ability to selectively deliver one or more therapeutic agents to a target tissue (e.g., tumor-associated antigen, such as CD73-expressing tumor), the immunoconjugate can enhance the therapeutic efficacy of the antibody or antigen-binding fragment thereof of the present invention to treat a disease (e.g., cancer).

Accordingly, in another aspect, the present invention provides an immunoconjugate, which comprises the antibody or antigen-binding fragment thereof of the present invention and a therapeutic agent linked to the antibody or antigen-binding fragment thereof.

In certain embodiments, the immunoconjugate is an antibody-drug conjugate (ADC).

In certain embodiments, the therapeutic agent is a cytotoxic agent. In the present invention, the cytotoxic agent includes any agent that is detrimental to a cell (e.g., kills cell).

In certain embodiments, the therapeutic agent is selected from the group consisting of alkylating agent, mitotic inhibitor, antineoplastic antibiotic, antimetabolite, topoisomerase inhibitor, tyrosine kinase inhibitor, radionuclide agent, and any combination thereof.

Examples of the alkylating agent that can be used in the immunoconjugate of the present invention include, but are not limited to, nitrogen mustards (e.g., mechlorethamine, chlorambucil, Melphalan, cyclophosphamide, etc.), ethyleneimine (e.g., thiotepa, etc.), sulfates and polyols (e.g., busulfan, dibromomannitol), nitrosoureas (e.g., carmustine, lomustine, etc.), platinum-based antitumor agents (e.g., cisplatin, oxaliplatin, carboplatin, etc.), etc.

Examples of mitotic inhibitor that can be used in the immunoconjugate of the present invention include, but are not limited to, maytansinoids (e.g., maytansine, maytansinol, C-3 ester of maytansinol, etc.), taxanes (e.g., docetaxel, paclitaxel or nanoparticle paclitaxel, etc.), vinca alkaloids (e.g., vindesine sulfate, vincristine, vinblastine or vinorelbine, etc.)

Examples of antitumor antibiotic that can be used in the immunoconjugate of the present invention include, but are not limited to, actinomycins, anthracyclines (e.g., daunorubicin, doxorubicin, epirubicin, idarubicin, etc.), calicheamicins, duocarmycin, etc.

Examples of antimetabolite that can be used in the immunoconjugate of the present invention include, but are not limited to, folate antagonists (e.g., methotrexate, etc.), pyrimidine antagonists (e.g., 5-fluorouracil, floxuridine, cytarabine, capecitabine, gemcitabine, etc.), purine antagonists (e.g., 6-mercaptopurine, 6-thioguanine, etc.), adenosine deaminase inhibitors (e.g., cladribine, fludarabine, nelarabine, pentostatin, etc.).

Examples of topoisomerase inhibitor that can be used in the immunoconjugate of the present invention include, but are not limited to camptothecins and derivatives thereof (e.g., irinotecan, topotecan, etc.), amsacrine, daunomycin, doxorubicin, epipodophyllotoxin, ellipticines, epirubicin, etoposide, razoxane, teniposide, etc.

Examples of tyrosine kinase inhibitor that can be used in the immunoconjugate of the present invention include, but are not limited to, axitinib, bosutinib, cediranib, dasatinib, erlotinib, gefitinib, imatinib, lapatinib, lestaurtinib, nilotinib, semaxanib, sunitinib, vandetanib, etc.

Examples of radionuclide agent that can be used in the immunoconjugate of the present invention include, but are not limited to, $I^{131}$, $In^{111}$, $Y^{90}$, $Lu^{177}$, and the like.

In certain exemplary embodiments, the therapeutic agent is selected from the group consisting of platinum-based antineoplastic agent, anthracycline, taxane compounds, nucleoside analog, camptothecin compounds, and analog or homolog thereof, and any combination thereof.

In certain embodiments, the antibody or antigen-binding fragment thereof of the present invention is optionally conjugated to the therapeutic agent via a linker.

In the present invention, a cytotoxic agent can be conjugated to the antibody or antigen-binding fragment thereof of the present invention using a linker technology available in the art. Examples of the types of linker that have been used to conjugate cytotoxic agent to antibody include, but are not limited to, hydrazone, thioether, ester, disulfide, and peptide-containing linker. The linker can be selected from those, for example, susceptible to cleavage by low pH or by protease (e.g., protease preferentially expressed in tumor tissue, such as cathepsin, such as cathepsin B, C, D) within the lysosomal compartment.

Further discussion on the types of cytotoxic agents, the linkers, and the methods of conjugating therapeutic agents to antibodies can also be seen in Saito, G. et al., (2003) Adv. Drug Deliv. Rev. 55:199-215; Trail, P. A. et al., (2003) Cancer Immunol. Immunother. 52: 328-337; Payne, G. (2003) Cancer Cell 3: 207-212; Allen, T. M. (2002) Nat. Rev. Cancer 2: 750-763; Pastan, I. and Kreitman, R. J. (2002) Curr. Opin. Investig. Drugs 3: 1089-1091; Senter, P. D. and Springer, C. J. (2001) Adv. Drug Deliv. Rev. 53: 247-264.

Therapeutic Use and Pharmaceutical Composition

The antibody or antigen-binding fragment thereof of the present invention can modulate (e.g., enhance, stimulate, increase, inhibit, decrease or neutralize) one or more biological activities of CD73. In certain instances, the antibody or antigen-binding fragment thereof of the present invention results in one or more of: inhibition or reduction of enzymatic activity of CD73; inhibition or reduction of the conversion of adenosine monophosphate (AMP) to adenosine; and increased proliferation of anti-CD3/anti-CD28 stimulated T cells (e.g., CD4+ T cells) in the presence of adenosine monophosphate (AMP). Therefore, the antibody or antigen-binding fragment thereof of the present invention can be used as a single drug to prevent and/or treat a tumor by inhibiting or reducing the enzymatic activity of CD73.

In addition, it has been reported that targeting CD73 may exhibit synergistic effects with other anticancer drugs. In a prospective randomized phase III clinical trial evaluating the activity of trastuzumab, high levels of CD73 gene expression were significantly associated with poor clinical outcomes; and in an immunocompetent mouse model of HER2/ErbB2-driven breast cancer, and the CD73 expression by tumor cells and host cells significantly inhibits immune responses mediated by anti-ErbB2 monoclonal antibodies (Martin T et al., Cancer Research 2017; 77(20); 5652-63). In addition, in vitro experiments have shown that activation of A2A receptors can regulate the upregulation of PD-1 on tumor-infiltrating cytotoxic T cells, while blocking PD-1 signaling with anti-PD-1 antibodies upregulates the expression of A2A receptors on tumor-infiltrating cytotoxic T cells (Cekic C et al., Cancer Res 2014; 74: 7239-49). Anti-CD73 antibodies have been reported to significantly enhance the activity of anti-CTLA-4 antibodies and anti-PD-1 antibodies in various mouse tumor models, and both monotherapy and combination therapy are dependent on host interferon γ and cytotoxic T cells; effects of extracellular adenosine on tumor-infiltrating T cells showed that receptor activation of adenosine enhances PD-1 expression on tumor-specific cytotoxic T cells and helper T cells (Bertrand A et al., Clin Cancer Res 2013; 19(20):5626-5635). Clinical studies have found that increased CD73 levels are positively correlated with disease progression in melanoma patients treated with Pembrolizumab (anti-PD-1). The relationship between dynamic up-regulation of CD73 and adaptive resistance to anti-PD-1 antibodies is noteworthy (Reinhardt J et al., Cancer Research 2017; 77: 4697-4709). Another study showed that high levels of soluble CD73 enzyme activity were significantly associated with poorer overall and progression-free survival in metastatic melanoma patients receiving nivolumab. In multivariate analysis, CD73 enzyme activity emerged as the strongest prognostic factor for overall survival and progression-free survival, and higher basal levels of CD73 enzyme activity prior to initiation of nivolumab were associated with lower rates of treatment response (Silvana M et al., J Transl Med 2017; 15:244). Correspondingly, the expression levels of CD73 and PD-L1 were also found to complement each other in tumor samples from patients with non-small cell lung cancer. It can be seen that the antibody or antigen-binding fragment thereof of the present invention can also be used in combination with immune checkpoint inhibitors or tumor-specific antibodies for the prevention and treatment of tumors.

Accordingly, in another aspect, the present invention provides a pharmaceutical composition, which comprises the antibody or antigen-binding fragment thereof, bispecific or multispecific molecule, or immunoconjugate of the present invention, and a pharmaceutically acceptable carrier and/or excipient.

In certain embodiments, the pharmaceutical composition may further comprise an additional pharmaceutically active agent.

In certain embodiments, the additional pharmaceutically active agent is a drug with antitumor activity, for example, alkylating agent, mitotic inhibitor, antitumor antibiotic, anti-metabolite, topoisomerase inhibitor, tyrosine kinase inhibitor, radionuclide agent, radiosensitizer (e.g., gemcitabine, 5-fluorouracil, taxane, cisplatin, etc.), anti-angiogenic agent, cytokine (e.g., GM-CSF, IL-7, IL-12, IL-15, IL-18, IL-21, etc.), molecular targeted drug (e.g., CD20 antibody, such as rituximab, Her2 antibody such as trastuzumab, VEGF antibody such as bevacizumab, EGFR antibody such as cetuximab, etc.), immune checkpoint inhibitor (e.g., PD-1 antibody, PD-L1 antibody, CTLA-4 antibody, LAG-3 antibody, etc.), oncolytic virus, etc.

In certain embodiments, the additional pharmaceutically active agent is selected from the group consisting of immune checkpoint inhibitor (e.g., PD-1 inhibitor, PD-L1 inhibitor, CTLA-4 inhibitor, LAG-3 inhibitor), anti-CD39 antibody, anti-A2AR antibody or anti-HER2/ErbB2 antibody.

In certain embodiments, in the pharmaceutical composition, the antibody or antigen-binding fragment thereof, bispecific or multispecific molecule, or immunoconjugate of the present invention and the additional pharmaceutically active agent are provided as isolated components or as a mixture. Thus, the antibody or antigen-binding fragment thereof, bispecific or multispecific molecule, or immunoconjugate of the present invention and the additional pharmaceutically active agent can be administered simultaneously, separately or sequentially.

In certain exemplary embodiments, the pharmaceutical composition comprises a sterile injectable liquid (e.g., aqueous or non-aqueous suspension or solution). In certain exemplary embodiments, such sterile injectable liquid is selected from the group consisting of water for injection (WFI), bacteriostatic water for injection (BWFI), sodium chloride solution (e.g., 0.9% (w/v) NaCl), dextrose solution (e.g., 5% dextrose), surfactant-containing solution (e.g., 0.01% polysorbate 20), pH buffered solution (e.g., phosphate buffered solution), Ringer's solution, and any combination thereof.

In another aspect, the present invention provides a method for preventing and/or treating a tumor in a subject (e.g., a human), the method comprising administering to a subject in need thereof an effective amount of the antibody or antigen-binding fragment thereof, bispecific or multispecific molecule, immunoconjugate or pharmaceutical composition of the present invention. In another aspect, there is provided a use of the antibody or antigen-binding fragment thereof, bispecific or multispecific molecule, immunoconjugate, or pharmaceutical composition of the present invention in the prevention and/or treatment of a tumor in a subject (e.g., a human), or in the manufacture of a medicament for the prevention and/or treatment of a tumor in a subject (e.g., a human).

In certain embodiments, the tumor expresses CD73. In certain embodiments, the CD73 can be membrane-bound human CD73 and/or soluble human CD73.

In certain embodiments, the tumor involves CD73-expressing tumor cell. In certain embodiments, the CD73 is expressed on the surface of the tumor cell.

In certain embodiments, the tumor is selected from the group consisting of melanoma, colon cancer, lung cancer, liver cancer, pancreatic cancer, ovarian cancer, bladder cancer, glioma, glioblastoma, thyroid cancer, esophageal cancer, prostate cancer and breast cancer.

In certain embodiments, the antibody or antigen-binding fragment thereof of the present invention is administered in combination with a second therapeutic agent or therapy. The second therapeutic agent or therapy can be administered before, concurrently with, or after the administration of the antibody or antigen-binding fragment thereof of the present invention.

In certain embodiments, the second therapeutic agent is selected from drugs with anti-tumor activity, such as alkylating agent, mitotic inhibitor, anti-tumor antibiotic, antimetabolite, topoisomerase inhibitor, tyrosine kinase inhibitor, radionuclide agent, radiosensitizer, anti-angiogenic agent, cytokine, molecular targeted drug, immune checkpoint inhibitor or oncolytic virus.

In certain embodiments, the antibody or antigen-binding fragment thereof of the present invention is administered in combination with a therapeutic agent selected from the group consisting of immune checkpoint inhibitor (e.g., PD-1 inhibitor, PD-L1 inhibitor, CTLA-4 inhibitor, LAG-3 inhibitor), anti-CD39 antibody, anti-A2AR antibody or anti-HER2/ErbB2 antibody.

In certain exemplary embodiments, the PD-1 inhibitor is selected from the group consisting of PDR001, nivolumab, pembrolizumab, pidilizumab, MEDI0680, REGN2810, TSR-042, PF-06801591 and AMP-224.

In certain exemplary embodiments, the PD-L1 inhibitor is selected from the group consisting of FAZ053, atezolizumab, avelumab, durvalumab, and BMS-936559.

In certain exemplary embodiments, the CTLA-4 inhibitor is selected from ipilimumab or tremelimumab.

In certain exemplary embodiments, the LAG-3 inhibitor is selected from the group consisting of LAG525, BMS-986016, TSR-033, MK-4280, and REGN3767.

In certain embodiments, the second therapy may be any therapy known to be used for tumor, such as surgery, chemotherapy, radiation therapy, targeted therapy, immunotherapy, hormone therapy, gene therapy, or palliative therapy.

In another aspect, the present invention provides a method for stimulating an immune response in a subject, the method comprising administering to a subject in need thereof an effective amount of the antibody or antigen-binding fragment thereof, bispecific or multispecific molecule, immunoconjugate or pharmaceutical composition of the present invention. In another aspect, there is provided a use of the antibody or antigen-binding fragment thereof, bispecific or multispecific molecule, immunoconjugate, or pharmaceutical composition of the present invention in stimulating an immune response in a subject, or in the manufacture of a medicament for stimulating an immune response in a subject.

In certain embodiments, the immune response is a T cell-mediated immune response.

In certain embodiments, the immune response is an immune response against a tumor (e.g., a CD73-expressing tumor). In certain embodiments, the subject has a tumor (e.g., a CD73-expressing tumor).

In certain embodiments, the immune response is an immune response against an immunogen. In such embodiments, the method further comprises administering an immunogen to the subject. In some embodiments, the immunogen is selected from a tumor-associated antigen (e.g., a protein, polypeptide, or carbohydrate molecule), tumor cell, dendritic cell sensitized by the antigen, and any combination thereof. In other embodiments, the immunogen is selected from an antigen (e.g., a protein, polypeptide, or carbohydrate molecule) associated with a pathogen (e.g., a virus), an inactivated or attenuated pathogen, a dendritic cell sensitized by the antigen, and any combination thereof.

In another aspect, the present invention provides a method of reducing an adenosine level in a CD73-expressing tumor cell, comprising contacting the cell with the antibody or antigen-binding fragment thereof, bispecific or multispecific molecule, immunoconjugate, or pharmaceutical composition of the present invention. In certain embodiments, the method is used to reduce an adenosine level in a CD73-expressing tumor cell in vitro, for a non-therapeutic purpose. In another aspect, there is provided a use of the antibody or antigen-binding fragment thereof, bispecific or multispecific molecule, immunoconjugate, or pharmaceutical composition of the present invention in reducing an adenosine level in a CD73-expressing tumor cell, or in the manufacture of a medicament for reducing an adenosine level in a CD73-expressing tumor cell.

The antibody or antigen-binding fragment thereof, bispecific or multispecific molecule, immunoconjugate, pharmaceutical composition of the present invention can be formulated into any dosage form known in the medical arts, for example, tablet, pill, suspension, emulsion, solution, gel, capsule, powder, granule, elixir, lozenge, suppository, injection (including injection, sterile powder for injection and concentrated solution for injection), inhalant, spray, etc. The preferred dosage form depends on the intended mode of administration and therapeutic use. The pharmaceutical composition of the present invention should be sterile and stable under the conditions of manufacture and storage. A preferred dosage form is an injection. Such injectable preparations can be sterile injectable solution. Sterile injectable solution can be prepared, for example, by incorporating the required amount of the antibody of the present invention in an appropriate solvent, optionally with other desired ingredient (including, but not limited to, pH adjusting agent, surfactant, adjuvant, ionic strength enhancer, isotonicity agent, preservative, diluent, or any combination thereof), followed by filter sterilization. In addition, sterile injectable solution can be prepared as a sterile lyophilized powder (e.g., by vacuum drying or freeze-drying) for ease of storage and use. Such sterile lyophilized powder can be dispersed in a suitable vehicle such as water for injection (WFI), bacteriostatic water for injection (BWFI), sodium chloride solution (e.g., 0.9% (w/v) NaCl), dextrose solution (e.g., 5% dextrose), surfactant-containing solution (e.g., 0.01% polysorbate 20), pH buffered solution (e.g., phosphate buffered solution), Ringer's solution, and any combination thereof.

Furthermore, the antibody or antigen-binding fragment thereof, bispecific or multispecific molecule, immunoconjugate, pharmaceutical composition of the present invention may be presented in a pharmaceutical composition in unit dosage form for ease of administration.

The antibody or antigen-binding fragment thereof, bispecific or multispecific molecule, immunoconjugate, pharmaceutical composition of the present invention can be administered by any suitable method known in the art, including but not limited to oral, buccal, sublingual, ocular, topical, parenteral, rectal, intrathecal, intracytoplasmic reticulum, inguinal, intravesical, topical (e.g., powder, ointment, or drop), or nasal route. However, for many therapeutic uses, the preferred route/mode of administration is parenteral (e.g., intravenous or bolus injection, subcutaneous injection, intraperitoneal injection, intramuscular injection). The skilled artisan will appreciate that the route and/or mode of administration will vary depending on the intended purpose. In a preferred embodiment, the antibody or antigen-binding fragment thereof, bispecific or multispecific molecule, immunoconjugate, pharmaceutical composition of the present invention is administered by intravenous injection or bolus injection.

The pharmaceutical composition of the present invention may comprise a "therapeutically effective amount" or "prophylactically effective amount" of the antibody or antigen-binding fragment thereof, bispecific or multispecific molecule, immunoconjugate, pharmaceutical composition of the present invention. The "prophylactically effective amount" refers to an amount sufficient to prevent, stop, or delay the onset of a disease. The "therapeutically effective amount" refers to an amount sufficient to cure or at least partially arrest a disease and complication thereof in a patient already suffering from the disease. The therapeutically effective amount of the antibody or antigen-binding fragment thereof of the present invention may vary according to the following factors: the severity of disease to be treated, the general state of the patient's own immune system, the general condition of the patient such as age, weight and sex, the drug's mode of administration, and an additional therapy administered concurrently, among others.

In the present invention, the dosage regimen can be adjusted to obtain the optimal response of interest (e.g., a therapeutic or prophylactic response). For example, a single dose may be administered, multiple doses may be administered over a period of time, or doses may be proportionally reduced or increased according to the exigencies of therapeutic situation.

In the present invention, the subject may be a mammal, such as a human.

Detection Use and Kit

The antibody or antigen-binding fragment thereof of the present invention can specifically bind to CD73, and thus can be used to detect the presence or level of CD73 in a sample.

Accordingly, in another aspect, the present invention provides a kit, which comprises the antibody or antigen-binding fragment thereof of the present invention. In some embodiments, the antibody or antigen-binding fragment thereof of the present invention bears a detectable label. In other embodiments, the kit further comprises a second antibody that specifically recognizes the antibody or antigen-binding fragment thereof of the present invention. Preferably, the second antibody further comprises a detectable label.

In certain embodiments, the detectable label is selected from the group consisting of enzyme (e.g., horseradish peroxidase), radionuclide, fluorescent dye, luminescent substance (e.g., chemiluminescent substance), or biotin.

In another aspect, the present invention provides a method for detecting the presence or amount of CD73 in a sample, comprising the steps of:

(1) contacting the sample with the antibody or antigen-binding fragment thereof of the present invention;

(2) detecting the formation of a complex between the antibody or antigen-binding fragment thereof and CD73 or detecting the amount of the complex.

The formation of the complex indicates the presence of CD73 or a cell expressing CD73.

In certain embodiments, the sample is a cellular sample, i.e., a sample comprising cells (e.g., tumor cells). In such embodiments, preferably, the complex is formed between the antibody or antigen-binding fragment thereof and the CD73 expressed by the cells in the sample.

In some embodiments, the antibody or antigen-binding fragment thereof of the present invention may further bear a detectable label. In other embodiments, in step (2), the antibody or antigen-binding fragment thereof of the present invention is detected using a reagent bearing a detectable label.

The method may be used for diagnostic purposes, or for non-diagnostic purposes (e.g., the sample is a cell sample rather than a sample from a patient). In certain embodiments, the CD73 is human CD73, for example, membrane-bound and/or soluble human CD73.

In another aspect, there is provided a use of the antibody or antigen-binding fragment thereof of the present invention for determining the presence or amount of CD73 in a sample, or in the manufacture of a kit for determining the presence or amount of CD73 in the sample. In certain embodiments, the CD73 is human CD73, for example, membrane-bound and/or soluble human CD73.

Definition of Terms

In the present invention, unless otherwise specified, scientific and technical terms used herein have the meanings commonly understood by those skilled in the art. In addition, the procedures of cell culture, biochemistry, nucleic acid chemistry, immunology laboratory, etc. used herein are all routine steps widely used in the corresponding fields. Meanwhile, for a better understanding of the present invention, definitions and explanations of related terms are provided below.

As used herein, the term "cluster of differentiation 73" or "CD73" is also referred to as extracellular-5'-nucleotidase, which is capable of converting extracellular 5' monophosphate nucleoside to nucleoside, i.e., adenosine monophosphate (AMP) is converted to adenosine. The term CD73 comprises a membrane-bound form (also known as membrane-bound CD73) or a soluble form (also known as soluble or non-membrane-bound CD73). CD73 can be isolated from cells or tissues in which they are naturally expressed, or produced recombinantly using techniques well known in the art. The sequence of CD73 is well known in the art and can be found in the NCBI database accession number NM_002526.

As used herein, the term "antibody" refers to an immunoglobulin molecule generally composed of two pairs of polypeptide chains (each pair having one light chain (LC) and one heavy chain (HC)). Antibody light chains can be classified as κ (kappa) and λ (lambda) light chains. Heavy chains can be classified as μ, δ, γ, α, or ε, and the isotypes of antibody can be defined as IgM, IgD, IgG, IgA, and IgE, respectively. In the light and heavy chains, the variable and constant regions are linked by a "J" region of about 12 or more amino acids, and the heavy chain also contains a "D" region of about 3 or more amino acids. Each heavy chain consists of a heavy chain variable region (VH) and a heavy chain constant region (CH). The heavy chain constant region consists of 3 domains (CH1, CH2 and CH3). Each light chain consists of a light chain variable region (VL) and a light chain constant region (CL). The light chain constant region consists of one domain, CL. Constant domain is not directly involved in the binding of antibody to antigen, but exhibits a variety of effector functions, such as mediating the binding of immunoglobulin to a host tissue or factor, including various cells (e.g., effector cells) of immune system and the first component (C1q) of classical complement system. The VH and VL regions can also be subdivided into regions of high variability (also called as complementarity determining regions (CDRs)), which are interspersed with more conserved regions called framework regions (FRs). Each $V_H$ and $V_L$ consists of 3 CDRs and 4 FRs arranged in the following order: FR1, CDR1, FR2, CDR2, FR3, CDR3, FR4 from amino terminus to carboxy terminus. The variable regions (VH and VL) of each heavy chain/light chain pair respectively form the antigen binding site. The assignment of amino acids to regions or domains can follow Kabat, Sequences of Proteins of Immunological Interest (National Institutes of Health, Bethesda, Md. (1987 and 1991)), or Chothia & Lesk (1987) J. Mol. Biol. 196: 901-917; definition by Chothia et al., (1989) Nature 342:878-883.

As used herein, the term "complementarity determining region" or "CDR" refers to the amino acid residues in an antibody variable region that are responsible for antigen binding. The variable regions of the heavy and light chains each contain three CDRs, designated CDR1, CDR2 and CDR3. The precise boundaries of these CDRs can be defined according to various numbering systems known in the art, for example according to the Kabat numbering system (Kabat et al., Sequences of Proteins of Immunological Interest, 5th Ed. Public Health Service, National Institutes of Health, Bethesda, Md., 1991), the Chothia numbering system (Chothia & Lesk (1987) J. Mol. Biol. 196:901-917; Chothia et al., (1989) Nature 342:878-883) or the IMGT numbering system (Lefranc et al., Dev. Comparat. Immunol. 27:55-77, 2003). For a given antibody, those skilled in the art will readily identify the CDRs defined by each numbering system. Also, correspondence between different numbering systems is well known to those skilled in the art (see, for example, Lefranc et al., Dev. Comparat. Immunol. 27:55-77, 2003).

In the present invention, the CDRs contained in the antibody or antigen-binding fragment thereof of the present invention can be determined according to various numbering systems known in the art. In certain embodiments, the CDRs contained in the antibody or antigen-binding fragment thereof of the present invention are preferably determined by the Kabat, Chothia or IMGT numbering systems. In certain embodiments, the CDRs contained in the antibody or antigen-binding fragment thereof of the present invention are preferably determined by the Kabat numbering system.

As used herein, the term "framework region" or "FR" residues refers to those amino acid residues in the variable region of antibody other than the CDR residues as defined above.

The term "antibody" is not limited by any particular method of producing an antibody. For example, it comprises recombinant antibody, monoclonal antibody and polyclonal antibody. The antibodies can be of different isotypes, for example, IgG (e.g., IgG1, IgG2, IgG3, or IgG4 subtype), IgA1, IgA2, IgD, IgE, or IgM antibody.

As used herein, the term "antigen-binding fragment" of antibody refers to a polypeptide comprising a fragment of full-length antibody that retains the ability to specifically bind to the same antigen to which the full-length antibody binds, and/or the compete with the full-length antibody to specifically bind to the antigen, which is also referred to as an "antigen binding moiety". See generally, Fundamental Immunology, Ch. 7 (Paul, W., ed., 2nd ed., Raven Press, N.Y. (1989), which is hereby incorporated by reference in its entirety for all purposes. The antigen-binding fragment of antibody can generate by recombinant DNA techniques or by enzymatic or chemical cleavage of intact antibody. Non-limiting examples of antigen-binding fragment include Fab, Fab', F(ab)$_2$, Fd, Fv, complementarity determining region (CDR) fragment, scFvs, diabody, single domain antibody, chimeric antibody, linear antibody, nanobody (technology from Domantis), and polypeptide comprising at least a part of antibody that is sufficient to confer specific antigen-binding ability to the polypeptide. Engineered antibody variants are reviewed in Holtiger et al., 2005; Nat Biotechnol, 23: 1126-1136.

As used herein, the term "full-length antibody" refers to an antibody consisting of two "full-length heavy chains" and two "full-length light chains". Wherein, "full-length heavy chain" refers to a polypeptide chain consisting of a heavy chain variable region (VH), a heavy chain constant region CH1 domain, a hinge region (HR), a heavy chain constant region CH2 domain, a heavy chain constant region CH3 domain in the direction from N-terminal to C-terminal; and optionally further comprising a heavy chain constant region CH4 domain in the case of IgE isotype. Preferably, the "full-length heavy chain" is a polypeptide chain consisting of VH, CH1, HR, CH2 and CH3 in the direction from N-terminal to C-terminal. The "full-length light chain" is a polypeptide chain consisting of a light chain variable region (VL) and a light chain constant region (CL) in the N-terminal to C-terminal direction. The two pairs of full-length antibody chains are linked together by a disulfide bond between CL and CH1 and a disulfide bond between the HRs of the two full-length heavy chains. The full-length antibody of the present invention can be from a single species, such as a human; it can also be a chimeric antibody or a humanized antibody. The full-length antibody of the present invention comprises two antigen-binding sites formed by VH and VL pairs, respectively, which specifically recognizes/binds to the same antigen.

As used herein, the term "Fd" refers to an antibody fragment consisting of VH and CH1 domains; the term "dAb fragment" refers to an antibody fragment consisting of VH domain (Ward et al., Nature 341:544 546 (1989)); the term "Fab fragment" refers to an antibody fragment consisting of VL, VH, CL and CH1 domains; the term "F(ab')₂ fragment" refers to an antibody fragment comprising two Fab fragments linked by a disulfide bridge on the hinge region; the term "Fab' fragment" refers to a fragment obtained by reducing the disulfide bond that links two heavy chain fragments in F(ab')₂ fragment, and consisting of an intact light chain and heavy chain Fd fragment (consisting of VH and CH1 domains).

As used herein, the term "Fv" refers to an antibody fragment consisting of VL and VH domains of one arm of antibody. Fv fragment is generally considered to be the smallest antibody fragment that can form an intact antigen-binding site. It is generally believed that the six CDRs confer antigen-binding specificity to an antibody. However, even a variable region (e.g., an Fd fragment, which contains only three antigen-specific CDRs) is able to recognize and bind to an antigen, albeit with possibly lower affinity than the intact binding site.

As used herein, the term "Fc" refers to an antibody fragment formed by binding the second and third constant regions of the first heavy chain to the second and third constant regions of the second heavy chain via a disulfide bond. The Fc fragment of antibody has many different functions, but is not involved in antigen binding.

As used herein, the term "scFv" refers to a single polypeptide chain comprising VL and VH domains, wherein the VL and VH are linked by a linker (see, for example, Bird et al., Science 242:423-426 (1988); Huston et al., Proc. Natl. Acad. Sci. USA 85:5879-5883 (1988); and Pluckthun, The Pharmacology of Monoclonal Antibodies, Vol. 113, Eds. Roseburg and Moore, Springer-Verlag, New York, pp. 269-315 (1994)). Such scFv molecule can have the general structure: NH₂-VL-linker-VH-COOH or NH₂-VH-linker-VL-COOH. A suitable linker in the prior art consists of repeated GGGGS amino acid sequences or variants thereof. For example, a linker with the amino acid sequence (GGGGS)₄, as well as variant thereof (Holliger et al. (1993), Proc. Natl. Acad. Sci. USA 90: 6444-6448) can be used. Other linkers useful in the present invention are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol. In some cases, a disulfide bond may also exist between the VH and VL of scFv.

As used herein, the term "diabody" refers to that its VH and VL domains are expressed on a single polypeptide chain, but the linker used is too short to allow pairing between the two domains of the same chain, this forces the domains to pair with the complementary domains of the other chain and create two antigen binding sites (see, for example, Holliger P. et al., Proc. Natl. Acad. Sci. USA 90:6444-6448 (1993), and Poljak R. J. et al., Structure 2:1121-1123 (1994)).

As used herein, the term "single-domain antibody (sdAb)" has the meaning commonly understood by those of skill in the art, which refers to an antibody fragment composed of a single monomeric variable antibody domain (e.g., a single heavy chain variable region) that retains the ability to specifically bind to the same antigen to which the full-length antibody binds. The single domain antibody is also known as nanobody.

Each of the aforementioned antibody fragments retains the ability to specifically bind to the same antigen to which the full-length antibody binds, and/or compete with the full-length antibody to specifically bind to the antigen.

The antigen-binding fragment of antibody (e.g., antibody fragment described above) can be obtained from a given antibody (e.g., an antibody provided herein) using conventional techniques known to those of skill in the art (e.g., recombinant DNA techniques or enzymatic or chemical fragmentation methods), and the antigen-binding fragment of antibody is screened specificity in the same manner as that used for the intact antibody.

Herein, unless the context clearly dictates otherwise, when the term "antibody" is referred to, it includes not only intact antibody but also antigen-binding fragment of antibody.

As used herein, the terms "monoclonal antibody", "McAb", "mAb" have the same meaning and are used interchangeably, and refer to one antibody or one fragment of antibody from a population of highly homologous antibody molecules, that is, a population of identical antibody molecules, except for natural mutations that may occur spontaneously. Monoclonal antibody is highly specific for a single epitope on an antigen. Polyclonal antibodies are relative to monoclonal antibody, which generally comprise at least two or more different antibodies that generally recognize different epitopes on an antigen. Furthermore, the modifier "monoclonal" only indicates that the antibody is characterized as being obtained from a population of highly homologous antibodies and should not be construed as requiring any particular method to prepare the antibody.

Monoclonal antibodies of the present invention can be prepared by a variety of techniques, such as hybridoma technology (see, for example, Kohler et al. Nature, 256:495, 1975), recombinant DNA technology (see, for example, U.S. Pat. No. 4,816,567), or bacteriophage antibody library technology (see, for example, Clackson et al., Nature 352: 624-628, 1991, or Marks et al., J. Mol. Biol. 222: 581-597, 1991).

Antibodies can be purified by well-known techniques, such as affinity chromatography using protein A or protein G. Subsequently or alternatively, the specific antigen (the target molecule recognized by the antibody) or its epitope can be immobilized on a column and the immunospecific antibody can be purified by immunoaffinity chromatography. For the purification of immunoglobulin, it may refer to, for example, D. Wilkinson (The Scientist, published by The Scientist, Inc., Philadelphia Pa., Vol. 14, No. 8 (Apr. 17, 2000), pp. 25-28).

As used herein, the term "chimeric antibody" refers to an antibody in which a portion of its light chain or/and heavy chain is derived from an antibody (which may be derived from a particular species or belong to a particular antibody class or subclass), and another portion of the light chain or/and heavy chain is derived from another antibody (which may be derived from the same or a different species or belong to the same or a different antibody class or subclass), however, it still retains the binding activity to the target antigen (U.S. Pat. No. 4,816,567 to Cabilly et al.; Morrison et al., Proc. Natl. Acad. Sci. USA, 81:6851 6855 (1984)). In certain embodiments, the term "chimeric antibody" may include such an antibody (e.g., a human-murine chimeric antibody) in which the heavy chain and light chain variable regions of the antibody are derived from a first antibody (e.g., a murine antibody), and the heavy chain and light chain constant regions of the antibody are derived from a second antibody (e.g., a human antibody).

As used herein, the term "humanized antibody" refers to a genetically engineered non-human antibody, of which the amino acid sequence has been modified to increase the homology to the sequence of a human antibody. Generally, all or part of the CDR regions of a humanized antibody are derived from a non-human antibody (donor antibody), and all or part of the non-CDR regions (e.g., variable FR and/or constant regions) are derived from a human immunoglobulin (receptor antibody). Typically, at least one or two, but usually all three, receptor CDRs (of heavy and/or light immunoglobulin chains) of a humanized antibody are replaced by donor CDRs. The immunoglobulin that provides the CDRs is called the "donor" and the immunoglobulin that provides the framework is called the "receptor". In one embodiment, the donor immunoglobulin is a non-human (e.g., murine) antibody, and the receptor framework can be a naturally occurring human framework sequence or have a sequence identity of about 85%, 90%, 95%, 99%, or higher as compared thereto. A humanized antibody generally retains the expected properties of the donor antibody, including, but not limited to, antigen specificity, affinity, reactivity, and the like. The donor antibody can be an antibody of mouse, rat, rabbit, or non-human primate (e.g., cynomolgus monkey) that has the expected properties (e.g., antigen specificity, affinity, reactivity, etc.).

In the present application, the expected properties of the antibody of the present invention include: (1) specific binding to CD73 (e.g., membrane-bound human CD73 or soluble human CD73); (2) inhibiting or reducing the enzymatic activity of CD73 (e.g., membrane-bound human CD73 or soluble human CD73); (3) increasing the proliferation of anti-CD3/anti-CD28 stimulated T cells (e.g., CD4+ T cells) in the presence of adenosine monophosphate (AMP); (4) mediating CD73 internalization; (5) reducing adenosine level in CD73-expressing tumor cells; (6) stimulating an immune response (e.g., an immune response to a tumor or immunogen); (7) preventing and/or treating a tumor (e.g., a CD73-expressing tumor). The antibody of the present invention possesses one or more of the expected properties described above.

The chimeric antibody or humanized antibody of the present invention can be prepared according to the sequence of the mouse monoclonal antibody prepared above. The DNA encoding the heavy and light chains can be obtained from target murine hybridoma and engineered to contain a non-murine (e.g., human) immunoglobulin sequence using standard molecular biology technique.

In order to prepare a chimeric antibody, a murine immunoglobulin variable region can be linked to a human immunoglobulin constant region using methods known in the art (see, for example, U.S. Pat. No. 4,816,567 to Cabilly et al.). For example, the DNA encoding VH is operably linked to another DNA molecule encoding the heavy chain constant region to obtain a full-length heavy chain gene. The sequences of human heavy chain constant regions gene are known in the art (see, for example, Kabat, E. A. et al. (1991), Sequences of Proteins of Immunological Interest, Fifth Edition, U.S. Department of Health and Human Services, NIH Publication No. 91-3242), and the DNA fragments containing these regions can be obtained by standard PCR amplification. The heavy chain constant region may be an IgG1, IgG2, IgG3, IgG4, IgA, IgE, IgM or IgD constant region, but is generally preferably an IgG1 or IgG4 constant region. For example, the DNA encoding VL is operably linked to another DNA molecule encoding the light chain constant region CL to obtain a full-length light chain gene (as well as a Fab light chain gene). The sequences of human light chain constant region genes are known in the art (see, for example, Kabat, E. A. et al. (1991), Sequences of Proteins of Immunological Interest, Fifth Edition, U.S. Department of Health and Human Services, NIH Publication No. 91-3242), and the DNA fragments containing these regions can be obtained by standard PCR amplification. The light chain constant region may be a κ or λ constant region, but is generally preferably a κ constant region.

In order to prepare a humanized antibody, a murine CDR region can be inserted into a human framework sequence using methods known in the art (see, U.S. Pat. No. 5,225,539 to Winter; U.S. Pat. Nos. 5,530,101; 5,585,089; 5,693,762 and 6,180,370 to Queen et al.; and Lo, Benny, K. C., editor, in Antibody Engineering: Methods and Protocols, volume 248, Humana Press, New Jersey, 2004). Alternatively, transgenic animals that are capable of producing complete human antibody repertoire without producing endogenous immunoglobulins after immunization can also be utilized. For example, it has been reported that the production of endogenous antibody could be completely suppressed by the homozygous deletion of the antibody heavy chain joining region (JH) gene in chimeric and germline mutant mice, then a human germline immunoglobulin gene array could be transferred to the germline mutant mice, and this could result in that the mice could produce a human antibody upon antigenic stimulation (see, for example, Jakobovits et al., 1993, Proc. Natl. Acad. Sci. USA 90:2551; Jakobovits et al., 1993, Nature 362: 255-258; Bruggermann et al., 1993, Year in Immunology 7: 33; and Duchosal et al., 1992, Nature 355: 258). Non-limiting examples of such transgenic animal include, HuMAb mouse (Medarex, Inc.), which contains a human immunoglobulin gene miniloci encoding unrearranged human heavy chains (μ and γ) and κ light chain immunoglobulin sequences, and additionally a targeted mutation that inactivates endogenous μ and κ chain loci (see, for example, Lonberg et al. (1994), Nature 368(6474):856-859); or "KM Mouse™" carrying a human heavy chain transgene and a human light chain transchromosome (see, patent application WO02/43478). Other methods of antibody humanization also include phage display technology (Hoogenboom et al., 1991, J. Mol. Biol. 227:381; Marks et al., J. Mol. Biol. 1991, 222:581-597; Vaughan et al., 1996, Nature Biotech 14:309).

As used herein, the term "germline antibody gene" or "germline antibody gene segment" refers to a sequence encoding immunoglobulin present in the genome of organism, which has not undergone a maturation process that leads to genetic rearrangement and mutation that result in the expression of specific immunoglobulin. In the present invention, the expression "heavy chain germline gene" refers to a germline antibody gene or gene fragment encoding an immunoglobulin heavy chain, which includes V gene (variable), D gene (diversity), and J gene (joining) and C gene (constant); similarly, the expression "light chain germline gene" refers to a germline antibody gene or gene fragment encoding an immunoglobulin light chain, which includes V gene (variable), J gene (joining) and C gene (constant). In the present invention, the amino acid sequence encoded by the germline antibody gene or germline antibody gene fragment is also referred to as "germline sequence", and the amino acid sequence encoded by the heavy chain germline gene is referred to as heavy chain germline sequence, the amino acid sequence encoded by the light chain germline gene is referred to as light chain germline sequence. Germline antibody genes or germline antibody gene fragments and their corresponding germline sequences are well known to those skilled in the art and can be obtained or queried from specialized databases (e.g., IMGT, UNSWIg, NCBI or VBASE2).

As used herein, the term "specific binding" refers to a non-random binding reaction between two molecules, such as between an antibody and the antigen to which it is directed. The strength or affinity of a specific binding interaction can be expressed in terms of the equilibrium dissociation constant ($K_D$) for that interaction. In the present invention, the term "$K_D$" refers to the dissociation equilibrium constant of a specific antibody-antigen interaction, which is used to describe the binding affinity between an antibody and an antigen. The smaller the equilibrium dissociation constant, the tighter the antibody-antigen binding and the higher the affinity between the antibody and the antigen. In certain embodiments, an antibody that specifically binds to an antigen (or an antibody specific for an antigen) refers to an antibody that binds to the antigen with an affinity ($K_D$) of less than about $10^{-9}$ M, such as less than about $10^{-9}$ M, $10^{-10}$ M, $10^{-11}$ M or $10^{-12}$ M or less. The specific binding properties between two molecules can be determined using methods well known in the art, for example using a BIACORE instrument by surface plasmon resonance (SPR) method.

As used herein, the term "cytotoxic agent" includes any agent that is detrimental to (e.g., kills) a cell, and examples thereof include chemotherapeutic drugs, bacterial toxins, plant toxins, or radioisotopes, and the like.

As used herein, the term "vector" refers to a nucleic acid delivery vehicle into which a polynucleotide can be inserted. When the vector can express the protein encoded by the inserted polynucleotide, the vector is called as an expression vector. The vector can be introduced into a host cell by transformation, transduction or transfection, so that the genetic material element carried thereby can be expressed in the host cell. Vectors are well known to those skilled in the art and include, but are not limited to: plasmids; phagemid; cosmid; artificial chromosome, such as yeast artificial chromosome (YAC), bacterial artificial chromosome (BAC) or P1 derived artificial chromosome (PAC); phage such as λ phage or M13 phage and animal virus. Animal viruses that can be used as vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40). A vector may contain a variety of elements that control expression, including, but not limited to, promoter sequence, transcription initiation sequence, enhancer sequence, selection element, and reporter gene. Additionally, the vector may also contain an origin of replication site.

As used herein, the term "host cell" refers to a cell into which a vector can be introduced, including, but not limited to, prokaryotic cell such as *E. coli* or *Bacillus subtilis*, fungal cell such as yeast cell or *Aspergillus*, etc., insect cell such as S2 *Drosophila* cell or Sf9, or animal cell such as fibroblast, CHO cell, COS cell, NSO cell, HeLa cell, BHK cell, HEK 293 cell or human cell.

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" refers to an amino acid substitution that does not adversely affect or alter the intended properties of the protein/polypeptide comprising the amino acid sequence. For example, a conservative substitution can be introduced by standard techniques known in the art such as site-directed mutagenesis and PCR-mediated mutagenesis. Conservative amino acid substitutions include substitutions of amino acid residues with amino acid residues that have similar side chains, e.g., substitution with residues that are physically or functionally similar to the corresponding amino acid residues (e.g., having similar size, shape, charge, chemical properties, including the ability to form covalent bonds or hydrogen bonds, etc.). Families of amino acid residues with similar side chains have been defined in the art. These families include those with basic side chain (e.g., lysine, arginine, and histidine), acidic side chain (e.g., aspartic acid, glutamic acid), uncharged polar side chain (e.g., glycine, asparagine, glutamine, serine, threonine, tyrosine, cysteine, tryptophan), non-polar side chain (e.g., alanine, valine, leucine, isoleucine, proline, phenylalanine, methionine), 13 branched side chain (e.g., threonine, valine, isoleucine), and aromatic side chain (e.g., tyrosine, phenylalanine, tryptophan, histidine). Therefore, it is preferred to replace the corresponding amino acid residue with another amino acid residue from the same side chain family. Methods for identifying conservative substitutions of amino acids are well known in the art (see, for example, Brummell et al., Biochem. 32:1180-1187 (1993); Kobayashi et al., Protein Eng. 12(10):879-884 (1999) and Burks et al., Proc. Natl Acad. Set USA 94:412-417 (1997), which are incorporated herein by reference).

The twenty conventional amino acids referred to herein have been written following conventional usage. See, for example, Immunology-A Synthesis (2nd Edition, E. S. Golub and D. R. Gren, Eds., Sinauer Associates, Sunderland, Mass. (1991)), which are incorporated herein by reference. In the present invention, the terms "polypeptide" and "protein" have the same meaning and are used interchangeably. And in the present invention, amino acids are generally represented by one-letter and three-letter abbreviations well known in the art. For example, alanine can be represented by A or Ala.

As used herein, the term "pharmaceutically acceptable carrier and/or excipient" refers to a carrier and/or excipient that is pharmacologically and/or physiologically compatible with the subject and the active ingredient. It is well known in the art (see, for example, Remington's Pharmaceutical Sciences. Edited by Gennaro AR, 19th ed. Pennsylvania: Mack Publishing Company, 1995) and includes, but is not limited to: pH adjuster, surfactant, adjuvant, ionic strength enhancing agent, diluent, agent for maintaining osmotic pressure, agent for delaying absorption, preservative. For example, the pH adjusting agent includes, but is not limited to, phosphate buffer. The surfactant includes, but is not limited to, cationic, anionic or nonionic surfactant, such as Tween-80. The ionic strength enhancing agent includes, but is not limited to, sodium chloride. The preservative includes, but is not limited to, various antibacterial and antifungal agent, such as p-hydroxy-benzoate ester, chloretone, phenol, sorbic acid, and the like. The agent for maintaining osmotic pressure includes, but is not limited to, sugar, NaCl, and the like. The agent for delaying absorption includes, but is not limited to, monostearate salt and gelatin. The diluent includes, but is not limited to, water, aqueous buffer (e.g., buffered saline), alcohol and polyol (e.g., glycerol), and the like. The preservative includes, but is not limited to, various antibacterial and antifungal agent, such as thimerosal, 2-phenoxyethanol, paraben, chloretone, phenol, sorbic acid, and the like. The stabilizer has the meaning commonly understood by those skilled in the art, which is capable of stabilizing the desired activity of the active ingredient in the drug, including but not limited to sodium glutamate, gelatin, SPGA, saccharide (e.g., sorbitol, mannitol, starch, sucrose, lactose, glucan, or glucose), amino acid (e.g., glutamic acid, glycine), protein (e.g., dry whey, albumin, or casein) or degradation product thereof (e.g., lactalbumin hydrolyzate), etc. In certain exemplary embodiments, the pharmaceutically acceptable carrier or excipient includes sterile injectable liquid (e.g., aqueous or non-aqueous suspension or solution). In certain exemplary embodiments, such sterile injectable liquid is selected from the group consisting of water for injection (WFI), bacteriostatic water for injection (BWFI), sodium chloride solution (e.g., 0.9% (w/v) NaCl), dextrose solution (e.g., 5% dextrose), surfactant-containing solutions (e.g., 0.01% polysorbate-20), pH buffered solution (e.g., phosphate buffered solution), Ringer's solution, and any combination thereof.

As used herein, the term "prevention" refers to a method performed to prevent or delay the occurrence of a disease or disorder or symptom (e.g., a tumor) in a subject. As used herein, the term "treatment" refers to a method performed to obtain a beneficial or desired clinical outcome. For the purposes of the present invention, a beneficial or desired clinical outcome includes, but is not limited to, alleviation of symptom, reduction in the extent of disease, stabilization (i.e., not worsening) of disease state, delaying or slowing the progression of disease, amelioration or remission of disease state, and relief of symptom (whether in part or in whole), whether detectable or undetectable. In addition, "treatment" can also mean prolonging survival as compared to expected survival if not receiving treatment.

As used herein, the term "subject" refers to a mammal, such as a primate, such as a human. In certain embodiments, the subject (e.g., a human) has a tumor (e.g., a CD73-expressing tumor), or is at a risk for the aforementioned disease.

As used herein, the term "effective amount" refers to an amount sufficient to obtain, or at least partially obtain, the desired effect. For example, an effective amount for preventing a disease (e.g., a tumor) refers to an amount sufficient to prevent, arrest, or delay the onset of the disease (e.g., tumor); an effective amount for treating a disease refers to an amount sufficient to cure or at least partially prevent the disease and complication thereof in a patient with the disease. Determining such effective amounts is well within the ability of those skilled in the art. For example, an effective amount for therapeutic use will depend on the severity of disease to be treated, the general state of patient's own immune system, the patient's general condition such as age, weight and sex, the mode of administration of drug, and other concurrently administered treatments and so on.

As used herein, the term "antibody-mediated internalization" refers to a phenomenon where an antibody passes through the cell membrane after binding to a cell surface antigen. Internalization includes antibody-mediated internalization of a receptor (e.g., CD73).

As used herein, the term "immune response" refers to an action of an immune cell (e.g., lymphocyte, antigen-presenting cell, phagocyte, or granulocyte) and a soluble macromolecule (including antibody, cytokine, and complement, etc.) produced by immune cells or liver, which result in a selective damage, destruction or clearance of an invasive pathogen, pathogen-infected cell or tissue, cancer cell, or normal human cell or tissue in autoimmune or pathological inflammatory conditions. In certain embodiments, the immune response refers to a T cell-mediated immune response that arises upon stimulation of the T cell by an antigen specific for the T cell. Non-limiting examples of the response produced by T cells upon antigen-specific stimulation include proliferation of T cells and production of cytokines.

Beneficial Effects of Invention

The antibody of the present invention can specifically bind to membrane-bound CD73 on the surface of tumor cells and soluble CD73, significantly inhibit the enzymatic activity of CD73, and enhance immune response. Thus, the antibody of the present invention has potential in use for the prevention and/or treatment of a tumor, particularly a CD73-expressing tumor. In addition, the humanized antibody of the present invention not only retains the functions and properties of the murine parent antibody, but also has a high degree of humanization, so that it can be safely administered to a human subject without eliciting an immunogenic response. It is especially surprising that the antibody of the present invention can more significantly restore the AMP-mediated CD4+ T cell suppression and enhance the killing effect on CD73-expressing tumor cells as compared to the known anti-CD73 antibodies. Therefore, the antibody (especially humanized antibody) of the present invention has great clinical value.

The embodiments of the present invention will be described in detail below with reference to the drawings and examples, but those skilled in the art will understand that the following drawings and examples are only used to illustrate the present invention, rather than limit the scope of the present invention. The various objects and advantageous aspects of the present invention will become apparent to those skilled in the art from the accompanying drawings and the following detailed description of the preferred embodiments.

SEQUENCE INFORMATION

Figure 1:
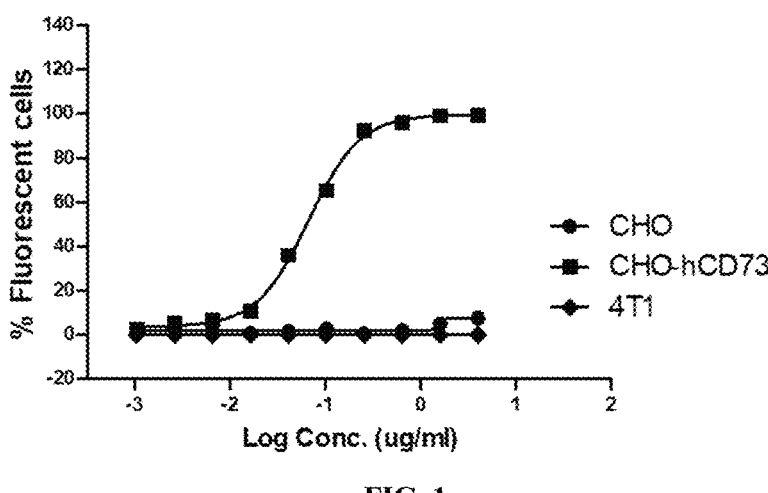
FIG. 1 shows the binding curve of murine antibody 13D12 to CD73 on the surface of tumor cells.

The information of the partial sequences involved in the present invention is provided as follows.

| SEQ ID NO | Description | Sequence information |
|---|---|---|
| 1 | 13D12 heavy chain variable region | DVKLQESGPAMVKPSQSLSLTCTVTGYSITSGYDWH WIRLFPGNKLEWMGYISYSGYTDYSPSLKSRISITHD TSKNHFFLKLHSVTTEDTATYYCTRGDHSYAMDYW GQGTSVTVS |
| 2 | 13D12 light chain variable region | DIVMTQSHKFMSTSVGDRVSITCKASQAVGTAVAW YQQKPGQSPKLLIYWASSRHTGVPDRFTGSRSGTDF TLTISSVQSEDLADYFCQQYSSYPLTFGGGTNLEIK |
| 3 | 13D12 HCDR1 | GYSITSGY |
| 4 | 13D12 HCDR2 | SYSGY |
| 5 | 13D12 HCDR3 | GDHSYAMDY |
| 6 | 13D12 LCDR1 | KASQAVGTAVA |
| 7 | 13D12 LCDR2 | WASSRHT |
| 8 | 13D12 LCDR3 | QQYSSYPLT |
| 9 | 7002-01 heavy chain variable region | QVQLQESGPGLVKPSQTLSLTCTVSGYSITSGYDWH WIRQHPGKGLEWMGYISYSGYTDYNPSLKSRITISHD TSKNQFSLKLSSVTAADTAVYYCTRGDHSYAMDYW GQGTLVTVSS |
| 10 | 7002-01 light chain variable region | AIQMTQSHSSLSASVGDRVTITCKASQAVGTAVAWY QQKPGKSPKLLIYWASSRHTGVPSRFSGSRSGTDFTL TISSLQPEDFATYFCQQYSSYPLTFGGGTKVEIK |
| 11 | 13D12 heavy chain variable region nucleic acid sequence | GATGTGAAGCTGCAGGAGAGCGGACCAGCTATGG TGAAGCCTAGCCAGAGCCTGAGCCTGACTTGCACC GTGACCGGCTACAGCATCACCAGCGGCTACGATTG GCATTGGATCAGACTGTTCCCAGGCAACAAGCTCG AGTGGATGGGCTACATCAGCTACAGCGGCTACAC CGACTACGACCCTAGCCTGAAGAGCCGGATCAGC ATCACCCACGACACCAGCAAGAACCACTTCTTCCT GAAGCTGCACAGCGTGACAACCGAGGACACCGCC ACCTACTATTGCACCAGAGGCGACCACAGCTACGC CATGGACTATTGGGGCCAGGGAACAAGCGTGACA GTGTCT |

-continued

| SEQ ID NO | Description | Sequence information |
|---|---|---|
| 12 | 13D12 light chain variable region nucleic acid sequence | GACATCGTGATGACCCAGAGCCACAAGTTCATGA GCACCAGCGTGGGAGACAGAGTGTCCATCACTTG CAAGGCCTCTCAGGCCGTGGGAACAGCCGTTGCTT GGTACCAGCAGAAGCCCGGACAGAGCCCCAAGCT GCTGATCTATTGGGCCAGCTCTAGACACACAGGAG TGCCAGACAGATTCACCGGCAGCAGAAGCGGAAC CGACTTCACCCTGACCATCAGCAGCGTGCAGAGCG AAGACCTGGCCGACTACTTCTGCCAGCAGTACAGC AGCTACCCCCTGACATTTGGCGGCGGCACCAACCT GGAGATCAAG |
| 13 | 7002-01 heavy chain variable region nucleic acid sequence | CAGGTCCAACTCCAAGAGAGCGGCCCCGGCCTCG TCAAACCCAGCCAAACACTCTCCCTCACCTGCACA GTCAGCGGCTACAGCATCACAAGCGGATACGACT GGCACTGGATCAGACAACACCCCGGCAAAGGCCT GGAGTGGATGGGCTATATCAGCTACAGCGGCTAC ACCGACTACAACCCAAGCCTGAAAAGCAGAATCA CAATCAGCCACGACACCAGCAAGAACCAGTTCAG CCTCAAGCTGAGCAGCGTGACCGCCGCAGACACC GCCGTCTACTATTGCACCAGAGGCGACCACTCCTA CGCCATGGACTACTGGGGCCAGGGCACCCTCGTG ACCGTGTCCAGC |
| 14 | 7002-01 light chain variable region nucleic acid sequence | GCTATTCAAATGACCCAGTCCCATTCCTCCCTGTC CGCCTCCGTGGGCGACCGAGTGACCATTACCTGTA AAGCCAGCCAAGCCGTCGGAACCGCCGTCGCATG GTACCAACAAAAACCCGGCAAAAGCCCCAAACTC CTCATCTACTGGGCCAGTAGCAGACACACCGGCGT GCCCAGCAGATTCAGCGGAAGCAGATCCGGCACC GACTTCACCCTGACCATCAGCAGCCTGCAACCCGA GGACTTCGCCACCTACTTCTGTCAGCAGTACAGCA GCTACCCCCTCACCTTCGGAGGCGGCACCAAGGTG GAGATCAAA |
| 15 | Human IgG1-TM heavy chain constant region | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSCDKTHTCP PCPAPEFEGGPSVFLFPPKPKDTLMISRTPEVTCVVV DVSHEDPEVKFNWYVDGVEVHNAKTKPREEQYNSTY RVVSVLTVLHQDWLNGKEYKCKVSNKALPASIEKTI SKAKGQPREPQVYTLPPSREEMTKNQVSLTCLVKGF YPSDIAVEWESNGQPENNYKTTPPVLDSDGSFFLYSK LTVDKSRWQQGNVFSCSVMHEALHNHYTQKSLSLS PGK |
| 16 | Human κ light chain constant region | RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |
| 17 | Human CD73 | MCPRAARAPATLLLALGAVLWPAAGAWELTILHTN DVHSRLEQTSEDSSKCVNASRCMGGVARLFTKVQQI RRAEPNVLLLDAGDQYQGTIWFTVYKGAEVAHFMN ALRYDAMALGNHEFDNGVEGLIEPLLKEAKFPILSA NIKAKGPLASQISGLYLPYKVLPVGDEVVGIVGYTSK ETPFLSNPGTNLVFEDEITALQPEVDKLKTLNVNKIIA LGHSGFEMDKLIAQKVRGVDVVVGGHSNTFLYTGN PPSKEVPAGKYPFIVTSDDGRKVPVVQAYAFGKYLG YLKIEFDERGNVISSHGNPILLNSSIPEDPSIKADINK WRIKLDNYSTQELGKTIVYLDGSSQSCRFRECNMGNLI CDAMINNNLRHTDEMFWNHVSMCILNGGGIRSPIDE RNNGTITWENLAAVLPFGGTFDLVQLKGSTLKKAFE HSVHRYGQSTGEFLQVGGIHVVYDLSRKPGDRVVK LDVLCTKCRVPSYDPLKMDEVYKVILPNFLANGGDG FQMIKDELLRHDSGDQDINVVSTYISKMKVIYPAVE GRIKFSTGSHCHGSFSLIFLSLWAVIFVLYQ |

EXAMPLES

The present invention will now be described with reference to the following examples, which are intended to illustrate, but not limit, the present invention.

Unless otherwise specified, the molecular biology experimental methods and immunoassays used in the present invention were performed basically by referring to J. Sambrook et al., Molecular Cloning: A Laboratory Manual, 2nd Edition, Cold Spring Harbor Laboratory Press, 1989, and F. M. Ausubel et al., Refined Molecular Biology Laboratory Manual, 3rd Edition, John Wiley & Sons, Inc., 1995; and restriction enzymes were used according to the conditions recommended by the product manufacturer. Those skilled in the art appreciate that the examples describe the present invention by way of example and are not intended to limit the scope sought to be protected by the present invention.

Example 1: Production of Murine Anti-Human CD73 Antibody

To obtain murine anti-human CD73 antibody, mice (Balb/c, Shanghai Lingchang Biotechnology) were immunized using different immunization strategies (Table 1). The antigens used included: CD73 protein (i.e., recombinantly expressed human CD73, with a sequence set forth in SEQ ID NO: 17) and CHOS-human CD73 (i.e., CHOS cell line that overexpressed CD73, which expressed CD73 with a sequence set forth in SEQ ID NO: 17); adjuvants included: complete Freund's adjuvant CFA (InvivoGen company, Cat. No.: vac-cfa-60), IFA (InvivoGen company, Cat. No.: vac-ifa-60), QuickAntibody (Beijing Boaolong Immune Technology Co. Ltd., Cat. No.: KX0210041); routes of administration included: intraperitoneal (ip) and subcutaneous (sc). Three days after boosting immunization, spleen cells of the immunized mice were fused with mouse myeloma cells SP2/0 using the polyethylene glycol method to obtain B cells that could express antibodies and could be indefinitely proliferated in vitro, and they were cultured in HAT selective medium. The fused hybridoma cells were plated on 96-well cell culture plate, and positive clones selected by primary screening were subjected to 2-3 rounds of subcloning.

TABLE 1

| | | Immunization strategies | | |
| Antigen | Dose | Adjuvant | Duration of immunization | Route of administration |
| --- | --- | --- | --- | --- |
| CD73 protein | 20 µg for each time | QuickAntibody | Once every 3 weeks, a total of 3 times | IP |
| CD73 protein & CHOS-human CD73 | 50 µg for the first time, then 20 µg for each time, using cells for FB | First CFA, then IFA | Once every 2 weeks, a total of 5 times | sc |
| CD73 protein | 50 µg for the first time, then 20 µg for each time | First CFA, then IFA | Once every 2 weeks, a total of 5 times | sc |
| CD73 protein & CHOS-human CD73 | 50 µg for the first time, then 20 µg for each time, using cells for FB | First CFA, then IFA | Once every 2 weeks, a total of 5 times | IP |
| CD73 protein | 50 µg for the first time, then 20 µg for each time | First CFA, then IFA | Once every 2 weeks, a total of 5 times | IP |

Primary screening: The binding abilities of culture supernatants of clones to CD73 on cell surface were determined in the primary screening by using human CD73-expressing tumor cells or overexpressing cell lines. The presence of the reactive antibody in the supernatants was revealed using the secondary antibody of DyLight488 goat anti-mouse IgG (Abeam Cat. No. ab97015), and the binding ability was assessed on a full-field cell scanning analyzer (see for detailed experimental procedures in Example 2). Secondary screening: CD73-expressing cells were used for screening for the ability to block CD73 enzyme activity to evaluate the antibody's ability to block CD73 enzyme activity on the cell membrane surface; human serum soluble CD73 was used for screening for the ability of blocking CD73 enzyme activity to evaluate the antibody's ability to block the soluble CD73 enzymatic activity (see for detailed experimental procedures in Example 6).

The mouse monoclonal antibody 13D12 was isolated and purified from the culture supernatant of the finally obtained positive hybridoma monoclonal cell line.

Example 2: Evaluation of Antigen-Binding Activity
of Murine Anti-CD73 Antibody 2.1 Detection of Binding of Murine Antibody to CD73
Positive Cells by Cell Scanning Analyzer Cells used: MDA-MB-231 (endogenously expressing human CD73; human breast cancer cell line), SK-ME-S (endogenously expressing human CD73; human lung squamous cell carcinoma cell line), H2030 (endogenously expressing human CD73; human non-small cell lung cancer cell line), SKLU1 (endogenously expressing human CD73; human lung adenocarcinoma cell line), BT549 (endogenously expressing human CD73; human breast ductal carcinoma cell line), A375 (endogenously expressing human CD73; human melanoma cell line), Calu6 (endogenously expressing human CD73; human degenerative cancer cell line), 4T1 (endogenously expressing murine CD73; murine breast cancer cell line), CHOS-human CD73 (transfected with human CD73) and CHOS (CD73 negative) cells.

Construction of CD73-expressing CHOS cells: Human CD73 (SEQ ID NO: 17) was overexpressed on CHOS cells (Invitrogen) by lentiviral infection and antibiotic resistance screening (MOI=3-10, 5 μg/ml polybrene). The lentivirus was provided by Shanghai Genechem Co., Ltd. After 72 hours of infection, the corresponding antibiotic was applied and culture was continued for 2 to 4 weeks, followed by expansion and cryopreservation for subsequent experiments.

Experimental method: 10,000 cells were plated on a flat-bottom 96-well plate with 100 μL DMEM+10% FBS/well, cultured overnight so that the cells adhered to the well, and the supernatant was discarded on the next day. Serial 3-fold dilutions of antibody for 8 points were performed by diluting ⅓ of the total volume (100 μL) in 200 μL DMEM. 100 μL of the diluted antibody was added to each well of the cell plate (the supernatants of fused clones or subclones were used for screening), 100 μL of DMEM was added to the corresponding negative control well, and incubation was performed at room temperature for 1 hour. After the supernatant was discarded, 100 μL of secondary antibody (DyLight488 goat anti-mouse IgG (Abcam, Cat. No. ab97015)) was added to each well at a concentration of 5 μg/mL (diluted in DMEM), and incubation was performed for 0.5 hours at room temperature. After staining, the supernatant was discarded, followed by washing once with PBS+ 2% FBS, then 100 μL of PBS+2% FBS was added to each well, and then reading was performed on analyzer. A full-field cell scanning analyzer (Nexcelom Company, model Celigo® Image Cytometer) was used to measure the reading of the experimental plate. During the measuring, high-speed scanning and imaging of the cells in the well was simultaneously performed in the green fluorescent channel corresponding to the secondary antibody and in the bright field channel. The image obtained by the fluorescence channel was used to count the cells bound by the antibody according to the parameters set for the morphology and fluorescence intensity of the fluorescently labeled cell, and image obtained by the brightfield channel was used to count the adherent cells according to the parameters set for cell morphology, and the percentage of the antibody-binding cells with fluorescence in the total number of cells was obtained by dividing the two counting results. The binding effect of the anti-CD73 antibody to the CD73-expressing cell line was determined according to the percentage. Graph-Pad was used for data analysis, wherein the abscissa indicated the logarithm of antibody concentration, the ordinate indicated the percentage of cells bound by CD73 antibody with green fluorescence in the total number of viable cells, and the EC50 values of the anti-CD73 antibody binding to each of the cells were obtained by curve fitting.

The EC50 values of 13D12 binding to each of the tumor cells were shown in Table 2-1 and Table 2-2, in which N.B. represented that it was not detected within the concentration range for detection; and the binding curves to some cells were shown in FIG. 1. The results showed that 13D12 could bind to cells naturally expressing CD73 and to CHOS cells recombinantly expressing human CD73, but the antibody did not bind to the cells that did not express CD73 (CHOS) nor to the cells expressing murine CD73 (4T1).

TABLE 2-1

| EC50 of antibody binding to tumor cells endogenously expressing human CD73 | | | | | | |
|---|---|---|---|---|---|---|
| | EC50 (ug/ml) | | | | | |
| Antibody | MDA-MB-231 | Calu6 | SK-ME-S | H2030 | SKLU1 | BT549 | A375 |
| 13D12 | 0.90 | 0.47 | 1.72 | 0.46 | 2.46 | 1.78 | 2.43 |

TABLE 2-2

| EC50 of antibody binding to CHOS cells recombinantly expressing human CD73 and to other cells not expressing human CD73 | | | |
|---|---|---|---|
| | EC50 (ug/ml) | | |
| Antibody | CHOS-human CD73 | CHOS | 4T1 |
| 13D12 | 0.44 | N.B. | N.B. |

2.2 Binding of Murine Antibody to Cynomolgus Macaques T Cells

Monkey blood samples from two donors (1132F and 1300M) were obtained from Medicilon. Peripheral blood mononuclear cells (PBMCs) were isolated using a Ficoll density gradient centrifugation system. The PBMCs were incubated with the antibody to be tested, then the antibodies bound on the cells were stained with fluorochrome-labeled secondary antibodies (DyLight488 goat anti-mouse IgG, Abcam Cat. No. ab97015; DyLight488 goat anti-human IgG, Abcam Cat. No. ab97003), and the fluorochrome-labeled antibodies against CD3+ and CD8+ were used to recognize T cells. Together with the unstained control samples and the fluorescence compensation control samples, all the samples were run on a flow cytometer to detect the binding of the antibodies to cynomolgus macaques T cells.

Figure 2:
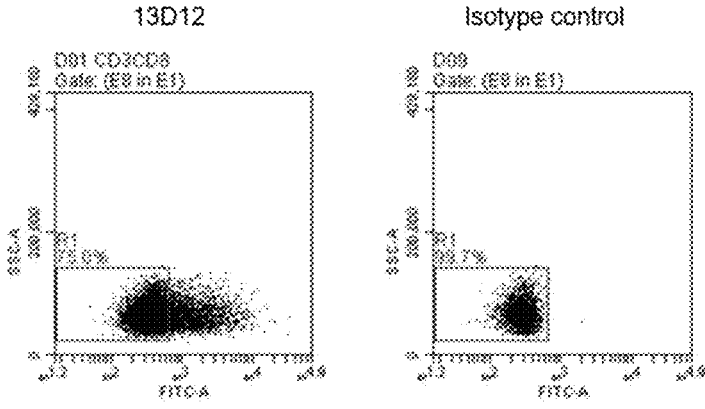
FIG. 2 shows the scatter binding plot of murine antibody 13D12 to monkey CD3+CD8+ T cells.

FIG. 2 showed a flow cytometry scatter plot of the binding of 13D12 to CD3+CD8+ T cells of cynomolgus macaques 1132F. The fold change of the mean fluorescence intensity for the binding of the murine antibody 13D12 was shown in the table below. The results showed that 13D12 was able to bind to cynomolgus macaques CD8+ T cells.

TABLE 3

| Binding of antibody to cynomolgus macaques PBMC | | |
|---|---|---|
| | MFI FC (ford change of mean fluorescence intensity) | |
| Antibody | 1132F | 1300M |
| 13D12 | 5.0 | 2.8 |
| Isotype control (IgG1-TM) | 1.2 | 1.0 |

Example 3: Determination of Variable Region Sequence of Murine Anti-CD73 Antibody and Preparation of Chimeric Antibody Hybridoma cells were collected by centrifugation, 5-10× $10^6$ cells were added with 1 ml of TRIzol and 0.2 ml of chloroform, vigorously shaken for 15 seconds, allowed to stand at room temperature for 3 minutes. After centrifugation, the aqueous phase was collected and added with 0.5 ml of isopropanol, allowed to stand at room temperature for 10 minutes. The precipitate was collected and washed with ethanol and dried to obtain RNA. Template RNA and primer were added to a centrifuge tube in ice-bath so that the primer and template paired correctly and then reverse transcription and PCR amplification were performed. 2.5 µl of dNTP/ddNTP mixture was added to each of 4 microcentrifuge tubes, and the mixture was at 37° C. for 5 min for later use. In an empty microcentrifuge tube, 1 pmol of PCR-amplified double-stranded DNA, 10 pmol of sequencing primer, and 2 µl of 5× sequencing buffer were added, and double-distilled water was added to reach a total volume of 10 µl, followed by heating at 96° C. for 8 min, cooling in ice-bath for 1 min, and centrifugation at 10000 g and 4° C. for 10 s. 2 µl of pre-chilled label mixture (dCTP, dGTP and dTTP, 0.75 µmol/L for each), 5 µCi of α-32P-dATP, 1 µl of 0.1 mol/L DDT, 2 U of sequencing enzyme were added, water was added to reach 15 µl, mixed well, and then allowed to stand on ice for 2 min, so as to label the newly synthesized DNA strands. 3.5 µl of the labeling reaction mixture was added to 4 previously prepared microcentrifuge tubes at 37° C. for 5 min. 4 µl of stop solution was added to each tube. The samples were heat-denatured in a water bath at 80° C. for 5 min, and 2 µl was added to each lane of sequencing gel, and the fragments were separated by electrophoresis to collect sequence information.

The VH and VL sequences of murine antibody 13D12 were shown in the table below. And the CDR sequences of murine monoclonal antibody 13D12 are further determined by the method described by Kabat et al. (Kabat et al., Sequences of Proteins of Immunological Interest, Fifth Edition, Public Health Service, National Institutes of Health, Bethesda, MD (1991), pp. 647-669).

TABLE 4

| Sequence information of murine antibody | | | | | | | | |
|---|---|---|---|---|---|---|---|---|
| | SEQ ID NO: | | | | | | | |
| Antibody | VH | VHCDR1 | VHCDR2 | VHCDR3 | VL | VLCDR1 | VLCDR2 | VLCDR3 |
| 13D12 | 1 | 3 | 4 | 5 | 2 | 6 | 7 | 8 |

The DNA sequences (SEQ ID NOs: 11-12) encoding the heavy chain and light chain variable regions of the above-mentioned murine antibody were ligated to the sequences encoding the heavy chain constant region (SEQ ID NO: 15) and light chain constant region (SEQ ID NO: 16) of human antibody, respectively, and recombinantly expressed in HEK293 cells (ATCC). The cell supernatants containing antibody clones in culture flask were collected, purified using protein A column, and the antibody protein was eluted with 100 mM acetic acid at pH 3.0. The purified antibody protein was then loaded onto a size exclusion chromatography column for further separation and purification. The antibody protein corresponding to monomer was formulated in a PBS buffer supplemented with 20% glycerol. Thus, chimeric antibody ch13D12 was obtained.

Example 4: Humanization of Murine Anti-CD73 Antibody

In order to improve the sequence homology between the candidate antibody and the human antibody, and to reduce the immunogenicity of the antibody to human, the design and preparation of humanization of the murine antibody provided in the above example were performed, in which the murine CDR regions were grafted into the human framework sequence by the method known in the art (see, U.S. Pat. No. 5,225,539 to Winter; U.S. Pat. Nos. 5,530,101; 5,585,089; 5,693,762 and 6,180,370 to Queen et al.; and Lo, Benny, K. C., editor, in Antibody Engineering: Methods and Protocols, volume 248, Humana Press, New Jersey, 2004).

Specifically, the heavy chain and light chain CDR regions of the murine antibody 13D12 were grafted to the FR framework of the corresponding humanized template, and a series of back mutations were performed on the amino acid residues of the FR region of the humanized template, so that the humanized antibody retained the antigen-binding ability of the murine antibody as much as possible. According to the above method, the present inventors prepared and obtained a humanized antibody of murine antibody 13D12, named as 7002-01 (its heavy chain variable region and light chain variable region were set forth in SEQ ID NOs: 9 and 10, respectively). The heavy chain constant region of the antibody was SEQ ID NO:15 and the light chain constant region was SEQ ID NO:16.

Example 5: Evaluation of Antigen-Binding Activity of Humanized Anti-CD73 Antibody 5.1 Determination of Antibody Binding to CD73-Expressing Cells by Flow Cytometry 500,000 CD73-expressing cells (see Example 2) were placed in 100 μL of FACS buffer (PBS+2% FBS)/well for later use in a round-bottom low adsorption 96-well plate. The antibody sample was subjected to serial 3-fold dilutions at 12 points by diluting ½ of the total volume (100 μL) in 200 μL of FACS buffer. 100 μL of the diluted antibody was added to each well of the cell plate, 100 μL of FACS buffer was added to the corresponding negative control well, and incubation was performed at 4° C. for 1 hour. After the supernatant was discarded by centrifugation, washing was performed twice with FACS buffer, 100 μL of secondary antibody (DyLight488 goat anti-mouse IgG, Abcam Cat. No. ab97015; DyLight488 goat anti-human IgG, Abcam Cat. No. ab97003) (5 μg/mL, diluted in FACS buffer) was added to each well, and incubation was performed at 4° C. for another 0.5 hours. After staining, the supernatant was removed by centrifugation, washing was performed twice with FACS buffer, and 100 μL of FACS buffer was added to each well to resuspend the cells, and then reading was performed on flow cytometry. The cells in the plate were measured using a flow cytometer (BD, model ACCURI C6 PLUS). During the measurement, the cells were first gated according to FCS and SSC, and then analyzed by the green fluorescence channel (FITC) corresponding to the secondary antibody and SSC. GraphPad was used for data analysis, wherein the abscissa indicated the logarithm of antibody concentration, the ordinate indicated mean fluorescence intensity, and the EC50 value of the anti-CD73 antibody was obtained by curve fitting. The binding of the humanized antibody 7002-01 to the cells naturally expressing CD73 and to the cells recombinantly expressing human CD73 was shown in Table 5, in which N.D. represented that no detection was performed. The results showed that the humanized antibody 7002-01 had good binding activity to membrane-bound CD73.

TABLE 5

| EC50 of antibody binding to tumor cells expressing human CD73 | | | | | | |
|---|---|---|---|---|---|---|
| | EC50 (ug/ml) | | | | | |
| Antibody | MDA-MB-231 | BT549 | A375 | H2030 | SKLU-1 | HCC44 | Calu6 |
| 7002-01 | 0.99 | N.D. | 0.60 | N.D. | N.D. | N.D. | N.D. |

Figure 3:
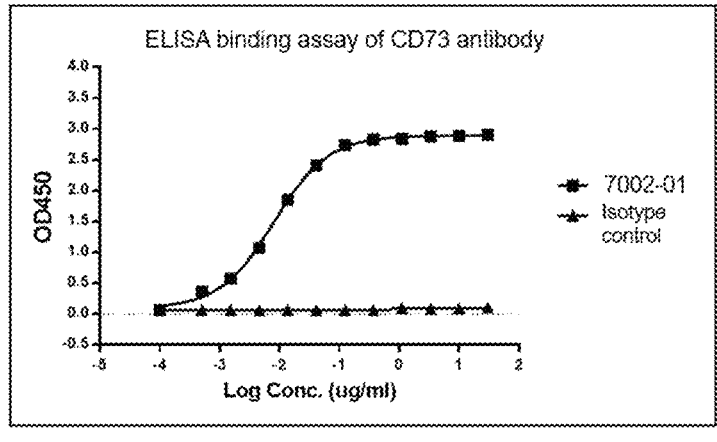
FIG. 3 shows the binding of humanized antibody 7002-01 to soluble recombinant CD73.

5.2 Determination of Antibody Binding to Soluble Human CD73 Protein by ELISA 1 µg/ml recombinant human CD73 protein (Baiying Bio, recombinant human CD73 protein) was coated on an ELISA plate in PBS for overnight at 4° C. The plate was washed 3 times with washing buffer (PBS, 0.05% Tween-20), and non-specific sites were blocked by adding 200 µl/well PBS+ 2% BSA. 100 µL of the anti-CD73 antibody in a dose range of gradient dilution was added to the ELISA plate coated with the antigen, and incubated at 37° C. for 1 h. The plate was washed 3 times in washing buffer, and HRP-coupled goat anti-human or goat anti-mouse IgG Fc fragment secondary antibody was added for 1 h at room temperature to detect the captured anti-CD73 antibody. The plate was washed 3 times with washing buffer, and the bound secondary antibody was revealed by adding TMB (HRP substrate) and incubating the plate for 5 to 10 minutes at room temperature in the dark. The enzymatic reaction was stopped by adding 1M sulfuric acid solution, and the light absorption was measured at 450 nm. The graph was plotted with the absorbance value on the ordinate and the log value of antibody concentration on the abscissa, and the EC50 was calculated using GraphPad Prism software. The results were shown in FIG. 3, indicating that the humanized antibody 7002-01 had good binding activity to soluble recombinant CD73, and the EC50 thereof was 0.0081 µg/ml.

5.3 Determination of Affinity of Humanized Antibody to Recombinant Human CD73 Protein by Biacore Antibody affinity was measured by SPR on Biacore T200 (GE) at 25° C. The antibody was diluted with running buffer 1*HBS-EP+ to 1 µg/ml, and was captured onto the chip surface (Protein A chip, GE, Cat #29127556) at a flow rate of 10 µl/min for 30 s. Then, a series of concentrations of CD73 protein (Baiying Bio, recombinant human CD73 protein) were injected into antibody channel at a flow rate of 30 µl/min, for association of 180 s, followed by dissociation for 900 s. 10 mM pH 1.5 Gly-HCl was used for regeneration. The sensorgram data was fitted using a 1:1 dynamic binding model. Bivalent affinity and kinetic association and dissociation rate constants were shown in the table below.

TABLE 6

Affinity constants of antibody binding to recombinant CD73

| Antibody | ka (1/Ms) | kd(1/s) | KD (M) |
|---|---|---|---|
| 7002-01 | 2.97E+05 | 6.24E−05 | 2.102E−10 |

Example 6: Evaluation of Inhibitory Activity of Anti-CD73 Antibody on CD73 Enzymatic Activity

6.1 Inhibition Assay of CD73 Enzymatic Activity in Tumor Cells

Excess AMP is known to block ATP-dependent luciferase activity. CD73, which cleaves AMP to adenosine+inorganic phosphate, restores luciferase activity and light emission by reducing AMP. Therefore, an antibody that blocks the enzymatic activity of CD73 will reduce light emission.

Human CD73-positive cells were harvested and counted, and seeded on a flat-bottom 96 plate, 20,000 cells per well in 100 µL of complete medium. The antibody sample was subjected to serial 3-fold dilutions at 8 points by diluting ⅓ of the total volume (100 µL) in 200 µL DMEM, 100 µL of the diluted samples were added to corresponding plate wells, and the negative control was the isotype control antibody (ISO). After incubation at 37° C. for 1 hour, the supernatant was removed and the cells were washed twice with PBS. A solution of AMP at a concentration of 125 µM was prepared in incomplete medium, 100 µL of AMP was added to each well, and the plate was incubated at 37° C. for an additional two hours. After the reaction plate was centrifuged, 50 µL of reaction solution was taken and added to another 96-well fluorescent plate (OptiPlate-96, Perkin Elmer, #6005290), added with the same volume of 50 µM ATP solution and 50 µL of CTG reagent (Promega, G7572) per well; the plate was incubated at room temperature in the dark for 15 minutes, and the fluorescence (Lum) was measured using a microplate reader. GraphPad was used for data analysis, the abscissa was the logarithm of antibody concentration, and the ordinate was the inhibition rate. The enzyme activity inhibition curve was drawn and IC50 was calculated. The inhibition rate was calculated as follows:

$$\text{Inhibition rate} = 100 - (\text{Lum}_{positive\ control} - \text{Lum}_{antibody}) / (\text{Lum}_{positive\ control} - \text{Lum}_{negative\ control}) * 100$$

The IC50 values of the antibody blocking endogenous CD73 in different human tumor cell lines were shown in the table below. The results showed that the humanized antibody 7002-01 could significantly inhibit the enzymatic activity of CD73 on the surface of tumor cells.

TABLE 7

IC50 of antibody inhibiting enzymatic activity of CD73 on surface of different human tumor cells

| | IC50 (ug/ml) | | | | | | |
|---|---|---|---|---|---|---|---|
| Antibody | MDA-MB-231 | BT549 | A375 | H2030 | SKLU-1 | HCC44 | Calu6 |
| 7002-01 | 1.00 | N.D. | 0.26 | N.D. | N.D. | N.D. | N.D. |

6.2 Inhibition Assay of CD73 Enzyme Activity in Tumor Patient Serum

The tumor patient serum was diluted in phosphate buffer (Tris 125 mM, MgCl₂ 25 mM, NaCl 125 mM), and 12.5 µL of diluted serum was added to each well for later use in white flat-bottom 96-well plate. The antibody sample was subjected to serial 2- to 10-fold dilutions at 10 points by diluting 1/1.5 of the total volume (100 µL) in 50 µL of phosphate buffer and by diluting 1/10 of the total volume (10 µL) in 90 µL of phosphate buffer. 12.5 µL of the diluted antibody was added to each well of the cell plate, and 12.5 µL of phosphate buffer was added as negative control, and incubation was performed at 37° C. for 1.5 hours after centrifugation. AMP was diluted with phosphate buffer to obtain into a 20 µM solution, 25 µL of AMP was added to each well (except for the positive control), and incubation was performed at 37° C. for another 1 hour after centrifugation. After the reaction, 25 µL of AMP was added to the positive control. 25 µL of AMP-Glo™ Reagent I (Promega, Cat. No. V5012) was immediately added to each well, the plate was centrifuged and incubated for 1 hour at room temperature. 50 μL of AMP Detection Solution (Promega, Cat. No. V5012) was added to each well and incubated at room temperature for 1 hour after centrifugation. Fluorescence (Lum) was measured using a microplate reader. GraphPad was used for data analysis, the abscissa was the logarithm of antibody concentration, and the ordinate was inhibition rate. The enzyme activity inhibition curve was drawn and IC50 was calculated. The inhibition rate was calculated as follows:

$$\text{Inhibition rate} = 100 - (\text{Lum}_{positive\ control} - \text{Lum}_{antibody}) / (\text{LUM}_{positive\ control} - \text{Lum}_{negative\ control}) * 100$$

Figure 4A:
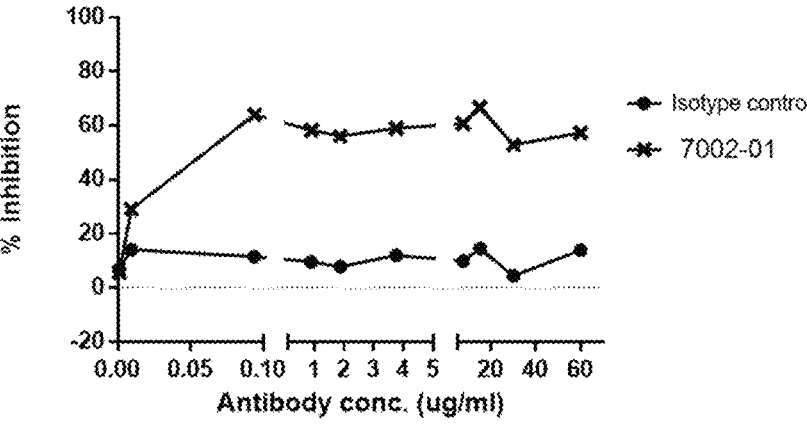
FIGS. 4A to 4B show the inhibition of CD73 enzyme activity by humanized antibody 7002-01 in sera of patients with liver cancer (A) and patients with melanoma (B).
Figure 4B:
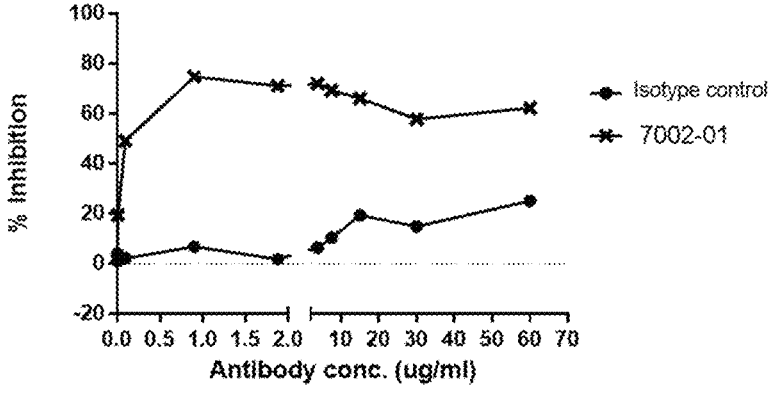

The results were shown in FIGS. 4A to 4B, indicating that the anti-CD73 antibody could effectively inhibit the dephosphorylation of AMP by CD73 in the serum samples of patients with liver cancer (A) and patients with melanoma (B), and inhibit the enzymatic activity of CD73.

Example 7: Anti-CD73 Antibody-Mediated Internalization of CD73

Anti-CD73 antibody-mediated internalization of CD73 was tested by flow cytometry. When determining the relationship between antibody-induced internalization and incubation time, the cells were incubated with 10 μg/mL antibody at 37° C. for various time periods. After washing several times with PBS containing 2% FBS, 10 μg/mL secondary antibody was added for staining at 4° C. for 30 minutes, and then the CD73 expression of the cells was analyzed by flow cytometry. When comparing differences in the degree of internalization caused by antibody, the cells were incubated with 10 μg/mL antibody for 20 hours in parallel at both 4° C. and 37° C. After washing several times with PBS containing 2% FBS, 10 μg/mL secondary antibody was added for staining at 4° C. for 30 minutes, and then the CD73 expression of the cells was analyzed by flow cytometry.

$MFI_{37}$ was the MFI value of the sample incubated at 37° C.; $MFI_4$ was the MFI value of the sample incubated at 4° C., and only binding occurs without internalization under this condition; and the $MFI_{background}$ was the MFI of the secondary antibody only. The percentage of antibody-mediated internalization of cell surface CD73 was calculated by the following formula:

$$\text{Percentage of internalized CD73} = 100 - 100 \times (MFI_4 - MFI_{37}) / MFI_4$$

The results were shown in Table 8, indicating that the antibody mediated the internalization of CD73 on the surface of tumor cells to varying degrees.

TABLE 8

| | | Percentage of antibody-mediated internalization of CD73 on surface of tumor cells | | | | | |
|---|---|---|---|---|---|---|---|
| Cell | Antibody | 6 hours | 4 hours | 2 hours | 1 hour | 0.5 hours | 0 hours |
| A375 | 7002-01 | 11% | 3% | 4% | 5% | 1% | 0% |
| MDA-MB-231 | 7002-01 | 8% | 4% | 4% | 3% | 5% | 0% |
| H2030 | 7002-01 | −1% | −2% | 4% | 1% | 6% | 0% |
| HCC44 | 7002-01 | 11% | 4% | 7% | 0% | 3% | 0% |
| Calu6 | 7002-01 | 13% | 7% | 6% | 3% | 7% | 0% |

Example 8: Anti-CD73 Antibody Relieving AMP-Mediated CD4+ T Cell Suppression PBMC cells (obtained from fresh apheresis sample by Ficoll separation) stimulated with anti-CD3/anti-CD28 for 24 hours before the experiment were collected and sorted using CD4+ T Cell Isolation Kit human (Miltenyi, Cat. No. 130-096-533) to obtain CD4+ T cells, followed by centrifugation to remove the supernatant. The CD4+ T cells were resuspended in AIMV medium containing 40 μM EHNA and 120 IU/ml IL2 (the final concentration of EHNA was 20 μM, and the final concentration of IL2 was 60 IU/ml). 200,000 CD4+ cells were plated in 100 μL/well in a low adsorption round-bottom 96-well plate. Serial 3-fold dilutions for 10 points were performed by diluting ⅓ of total volume (100 μL) in 200 μL of AIMV medium. 50 μL of the diluted antibody was added to each well, and 50 μL of AIMV medium was added to the corresponding negative control well, and incubation was performed at 37° C. for 0.5 hour. 400 μM AMP was prepared with AIMV to reach a final concentration of 100 μM, and 50 μL of the prepared AMP solution was added to each well (the control well was added with AMP-free medium). Reading was performed on analyzer after centrifugation. The plate was then incubated at 37° C. for 72 hours and then read again on analyzer. Readings were measured on cells in the plate using a full-field cell scanning analyzer (Nexcelom, model Celigo® Image Cytometer). During the measurement, high-speed scanning imaging of the cells in the well was performed in the brightfield channel. The effect of the anti-CD73 antibody alleviating the AMP-mediated CD4+ T cell suppression was determined based on the size of the clone cluster. MEDI9447 (MedImmune) and BMS986179 (BMS) were used as reference antibodies, which were expressed and purified by Genechem.

Figure 5:
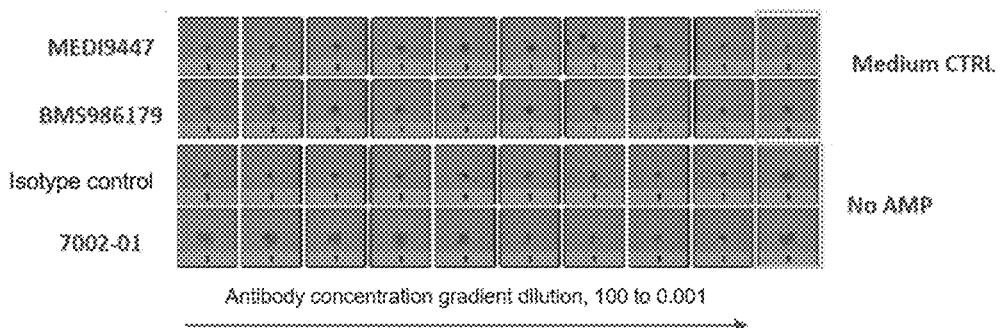
FIG. 5 shows the alleviating effect of humanized antibody 7002-01 on AMP-mediated CD4+ T cell suppression.

The cell growth on the $4^{th}$ day of T cell proliferation was shown in FIG. 5, in which #18 referred to the number of the PBMC donor for internal use, and the initial concentration of the antibody in the figure was 100 μg/mL, with a total of 9 points for 4-fold dilutions. The humanized antibody 7002-01 could effectively alleviate the AMP-mediated CD4+ T cell suppression, and the proliferation of T cells was significantly restored, and the effect was better than those of the reference antibodies MEDI9447 and BMS986179.

Example 9: Anti-CD73 Antibody-Mediated Tumor Cell Killing

5000 A375 cells were plated in 100 μL DMEM+10% FBS/well, in a flat-bottom 96-well plate. The cells were allowed to adhere overnight, and the supernatant was removed on the next day. Serial 3-fold dilutions for 10 points were performed by diluting ⅓ of total volume (100 μL) in 200 μL of AIMV. 50 μL of the diluted antibody was added to each well of the cell plate, 50 μL of AIMV was added to the corresponding negative control well, and incubation was performed at 37° C. for 0.5 hours. PBMC cells (from fresh apheresis sample by Ficoll separation) stimulated with anti-CD3/CD28 for 24 hours were collected, resuspended with AIMV containing 40 μM EHNA and 120 IU/ml IL2 (EHNA final concentration was 20 μM, IL2 final concentration was 60 IU/ml), and added to each well at 5,000/100 μL. AMP solution of 400 μM was prepared with AIMV, and 50 μL of the solution was added to each well to reach a final AMP concentration of 100 μM. Incubation was performed at 37° C. for 72 hours after centrifugation. 10 μL of CCK8 kit (Japan Dojindo Co., Ltd., Cat. No. CK04) was added to each well, incubated at 37° C. for 4 hours, and then OD450 was measured using a microplate reader. According to the value of the control well, the OD value was converted into the inhibition percentage, and the anti-CD73 antibody-mediated tumor cell killing effect was determined accordingly. The percentage is larger, the anti-CD73 anti-mediated tumor cell killing effect is better, and the percentage is smaller, the anti-CD73 anti-mediated tumor cell killing effect is worse. GraphPad was used for data analysis, the abscissa was the logarithm of antibody concentration, and the ordinate was the inhibition percentage, and the IC50 value of the anti-CD73 antibody on A375 cells was obtained by curve fitting.

Figure 6:
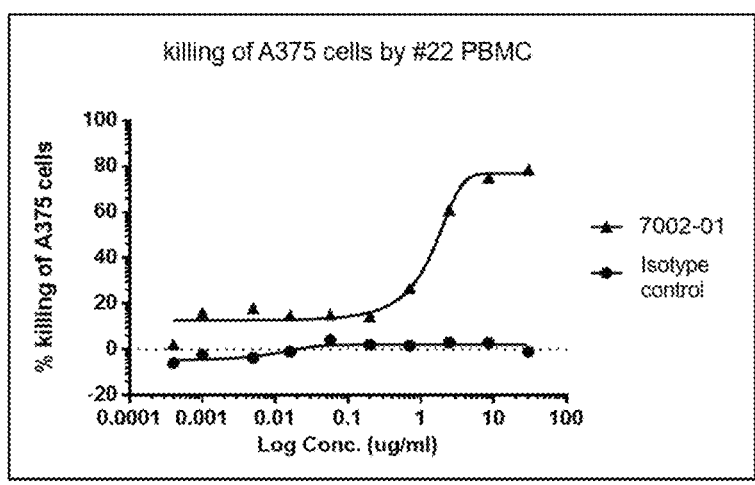
FIG. 6 shows the recovery effect of humanized antibody 7002-01 on the killing of tumor cells by PBMC.

The results were shown in FIG. 6, in which #22 referred to the donor number of PBMC for internal use. The results showed that the humanized antibody 7002-01 could effectively restore the killing effect of PBMC to tumor cells.

Although specific embodiments of the present invention have been described in detail, those skilled in the art will appreciate that various modifications and changes can be made to the details in light of all the teachings that have been published, and that these changes are all within the scope of the present invention. The full division of the present invention is given by the appended claims and any equivalents thereof.

---

What is claimed is:

1. An antibody or antigen-binding fragment thereof capable of specifically binding to CD73, the antibody or antigen-binding fragment thereof comprising a heavy chain variable region (VH) and a light chain variable region (VL), wherein:

(1) the VH comprises: VHCDR1 comprising the sequence set forth in SEQ ID NO: 3, VHCDR2 comprising the sequence set forth in SEQ ID NO: 4, VHCDR3 comprising the sequence set forth in SEQ ID NO: 5 and the VL comprises: VLCDR1 comprising a sequence set forth in SEQ ID NO: 6, VLCDR2 comprising the sequence set forth in SEQ ID NO: 7, and VLCDR3 comprising the sequence set forth in SEQ ID NO: 8 or, (2) the VH comprises three CDRs of the heavy chain variable region as shown in SEQ ID NO: 1; and the VL comprises three CDRs of the light chain variable region as shown in SEQ ID NO: 2; wherein the CDRs are defined by the Kabat, Chothia or IMGT numbering system.

2. The antibody according to claim 1, wherein the VH comprises the amino acid sequence set forth in SEQ ID NO: 1 or a sequence having a sequence identity of at least about 85%, 90%, 95% or 99% as compared thereto, and the VL comprises the amino acid sequence set forth in SEQ ID NO: 2 or a sequence having a sequence identity of at least about 85%, 90%, 95% or 99% as compared thereto.

3. The antibody or antigen-binding fragment thereof according to claim 1, wherein the antibody or antigen-binding fragment thereof comprises a framework region sequence derived from a human immunoglobulin;

or, the antibody or antigen-binding fragment thereof comprises a heavy chain framework region sequence derived from a human heavy chain germline sequence, and a light chain framework region sequence derived from a human light chain germline sequence.

4. The antibody or antigen-binding fragment thereof according to claim 3, wherein the VH comprises the amino acid sequence set forth in SEQ ID NO: 9 or a sequence having a sequence identity of at least about 85%, 90%, 95% or 99% as compared thereto, and the VL comprises the amino acid sequence set forth in SEQ ID NO: 10 or a sequence having a sequence identity of at least about 85%, 90%, 95% or 99% as compared thereto.

5. The antibody or antigen-binding fragment thereof according to claim 1, wherein the antibody or antigen-binding fragment thereof further comprises a constant region derived from a human immunoglobulin.

6. The antibody or antigen-binding fragment thereof according to claim 1, wherein the antigen-binding fragment is selected from the group consisting of Fab, Fab', (Fab')₂, Fv, disulfide-linked Fv, scFv, and diabody.

7. The antibody or antigen-binding fragment thereof according to claim 1, wherein the antibody is a murine antibody, a chimeric antibody, a humanized antibody, a bispecific antibody or a multispecific antibody.

8. The antibody or antigen-binding fragment thereof according to claim 1, wherein the antibody or antigen-binding fragment thereof possesses one or more of the following characteristics:

(a) binding to membrane-bound human CD73 or soluble human CD73 or both;

(b) inhibiting or reducing an enzymatic activity of membrane-bound human CD73 or soluble human CD73;

(c) increasing proliferation of CD4+ T cell stimulated by anti-CD3 and anti-CD28 antibodies in the presence of adenosine monophosphate (AMP);

(d) reducing an adenosine level in a CD73-expressing tumor cell;

(e) inducing internalization of CD73 into a cell by antibody-mediated receptor internalization.

9. A bispecific or multispecific molecule, which comprises the antibody or antigen-binding fragment thereof according to claim 1.

10. An immunoconjugate, which comprises the antibody or antigen-binding fragment thereof according to claim 1 and a therapeutic agent linked to the antibody or antigen-binding fragment thereof.

11. A pharmaceutical composition, which comprises the antibody or antigen-binding fragment thereof according to claim 1, a bispecific or multispecific molecule comprising the antibody or antigen-binding fragment thereof, or an immunoconjugate comprising the antibody or antigen-binding fragment thereof and a therapeutic agent linked thereto, and a pharmaceutically acceptable carrier and/or excipient.

12. A kit, which comprises the antibody or antigen-binding fragment thereof according to claim 1; wherein:

(i) the antibody or antigen-binding fragment thereof bears a detectable label; or (ii) the kit further comprises a second antibody, which specifically recognizes the antibody or antigen-binding fragment thereof; and the second antibody further comprises a detectable label.

13. A method for treating a tumor expressing CD73 in a subject, the method comprising administering to the subject an effective amount of the antibody or antigen-binding fragment thereof according to claim 1, a bispecific or multispecific molecule comprising the antibody or antigen-binding fragment thereof, an immunoconjugate comprising the antibody or antigen-binding fragment thereof and a therapeutic agent linked thereto, or a pharmaceutical composition comprising the antibody or antigen-binding fragment thereof, the bispecific or multispecific molecule or the immunoconjugate.

14. The method according to claim 13, wherein the method further comprises administering a second therapeutic agent with anti-tumor activity, or a second therapy selected from surgery, chemotherapy, radiation therapy, targeted therapy, immunotherapy, hormone therapy, gene therapy, or palliative care.

15. A method for stimulating an immune response in a subject, the method comprising administering to the subject an effective amount of the antibody or antigen-binding fragment thereof according to claim 1, or a pharmaceutical composition comprising the antibody or antigen-binding fragment thereof.

16. A method of detecting the presence or amount of CD73 in a sample, comprising the steps of:

(1) contacting the sample with the antibody or antigen-binding fragment thereof according to claim 1;

(2) detecting the formation of a complex between the antibody or antigen-binding fragment thereof and CD73 or detecting an amount of the complex.

17. The antibody according to claim 1, characterized by one or more of the following:

(i) the heavy chain of the antibody or antigen-binding fragment thereof comprises a IgG1, IgG2, IgG3 or IgG4 heavy chain constant region derived from a human immunoglobulin;

(ii) the light chain of the antibody or antigen-binding fragment thereof comprises a κ or λ light chain constant region derived from a human immunoglobulin;

(ii) the antibody or antigen-binding fragment thereof comprises a heavy chain constant region selected from: (1) a human IgG1 heavy chain constant region; (2) a variant of human IgG1 heavy chain constant region, which has the following substitution compared to the wild-type sequence from which it is derived: L234F, L235E, P331S, the amino acid positions mentioned above are positions according to the EU numbering system;

(iii) the antibody or antigen-binding fragment thereof comprises a heavy chain constant region (CH) set forth in SEQ ID NO: 15;

(iv) the antibody or antigen-binding fragment thereof comprises a light chain constant region (CL) set forth in SEQ ID NO: 16.

18. The pharmaceutical composition according to claim 11, characterized by one or more of the following:

(i) the pharmaceutical composition further comprises an additional pharmaceutically active agent with antitumor activity;

(ii) the pharmaceutical composition further comprises an additional pharmaceutically active agent selected from alkylating agent, mitotic inhibitor, antitumor antibiotic, antimetabolite, topoisomerase inhibitor, tyrosine kinase inhibitor, radionuclide agent, radiosensitizer, anti-angiogenic agent, cytokine, molecularly targeted drug, immune checkpoint inhibitor or oncolytic virus;

(iii) the pharmaceutical composition further comprises an additional pharmaceutically active agent selected from PD-1 inhibitor, PD-L1 inhibitor, CTLA-4 inhibitor, LAG-3 inhibitor, anti-CD39 antibody, anti-A2AR antibody or anti-HER2/ErbB2 antibody.

19. The method of claim 13, characterized by one or more of the following:

(i) the tumor is selected from the group consisting of melanoma, colon cancer, lung cancer, liver cancer, pancreatic cancer, ovarian cancer, bladder cancer, glioma, glioblastoma, thyroid cancer, esophageal cancer, prostate cancer and breast cancer;

(ii) the subject is a human.

20. The method of claim 13, the method comprises administering the antibody or antigen-binding fragment thereof in combination with an agent selected from the group consisting of PD-1 inhibitor, PD-L1 inhibitor, CTLA-4 inhibitor, LAG-3 inhibitor, anti-CD39 antibody, anti-A2AR antibody or anti-HER2/ErbB2 antibody.

\* \* \* \* \*